(12) United States Patent
Austin et al.

(10) Patent No.: US 12,101,604 B2
(45) Date of Patent: Sep. 24, 2024

(54) SYSTEMS, DEVICES AND METHODS FOR FITTING HEARING ASSISTANCE DEVICES

(71) Applicant: Starkey Laboratories, Inc., Eden Prairie, MN (US)

(72) Inventors: William F. Austin, Eden Prairie, MN (US); David Alan Fabry, Eden Prairie, MN (US); Justin R. Burwinkel, Eden Prairie, MN (US); Jeffrey Paul Solum, Greenwood, MN (US); Chris Howes, Eden Prairie, MN (US); Manfred Stoifl, Singapore (SG)

(73) Assignee: Starkey Laboratories, Inc., Eden Prairie, MN (US)

( * ) Notice: Subject to any disclaimer, the term of this patent is extended or adjusted under 35 U.S.C. 154(b) by 180 days.

(21) Appl. No.: 17/635,612

(22) PCT Filed: Aug. 13, 2020

(86) PCT No.: PCT/US2020/046179
§ 371 (c)(1),
(2) Date: Feb. 15, 2022

(87) PCT Pub. No.: WO2021/030584
PCT Pub. Date: Feb. 18, 2021

(65) Prior Publication Data
US 2022/0369053 A1 Nov. 17, 2022

(51) Int. Cl.
*H04R 25/00* (2006.01)
*A61B 5/00* (2006.01)
*A61B 5/12* (2006.01)

(52) U.S. Cl.
CPC .............. *H04R 25/70* (2013.01); *A61B 5/123* (2013.01); *A61B 5/4842* (2013.01);
(Continued)

(58) Field of Classification Search
None
See application file for complete search history.

(56) References Cited

U.S. PATENT DOCUMENTS 2,112,569 A 3/1938 Lybarger
3,095,483 A 6/1963 Tresise et al.
(Continued)

FOREIGN PATENT DOCUMENTS

WO 2021030584 2/2021

OTHER PUBLICATIONS

Hengen et al, "Perceived Voice Quality and Voice-Related Problems Among Older Adults With Hearing Impairments." https://pubs.asha.org/doi/abs/10.1044/2018_JSLHR-S-17-0383 Sep. 19, 2018. pp. 1-3 (Year: 2018).*

(Continued)

*Primary Examiner* — Qin Zhu
(74) *Attorney, Agent, or Firm* — Pauly, DeVries Smith & Deffner LLC

(57) ABSTRACT

Embodiments herein relate to systems, devices and methods for fitting hearing assistance devices. In a first aspect, a method of fitting a hearing assistance device is included, the method including providing an audio sample to a hearing assistance device wearer, receiving input from the hearing assistance device wearer regarding a preferred sound volume or perceived loudness, receiving input from the hearing assistance device wearer with the external device regarding a bass/treble balance, and determining a maximum power output of the hearing assistance device that does not exceed a loudness discomfort level (LDL). Other embodiments are also included herein.

20 Claims, 17 Drawing Sheets

(52) U.S. Cl.
CPC ......... *H04R 25/305* (2013.01); *H04R 25/505* (2013.01); *H04R 25/552* (2013.01); *H04R 25/554* (2013.01); *H04R 25/558* (2013.01); *H04R 2225/39* (2013.01); *H04R 2225/55* (2013.01); *H04R 2225/61* (2013.01)

(56) References Cited

U.S. PATENT DOCUMENTS

| | | | |
|---|---|---|---|
| 3,140,363 | A | 7/1964 | Barrows |
| 4,548,082 | A | 10/1985 | Engebretson et al. |
| 8,526,650 | B2 | 9/2013 | Fitz |
| 8,761,422 | B2 | 6/2014 | Fitz et al. |
| 9,326,706 | B2 | 5/2016 | Shennib |
| 10,341,790 | B2 | 7/2019 | Shennib |
| 10,412,515 | B2 * | 9/2019 | Flynn ............... H04R 25/356 |
| 2003/0002698 | A1 * | 1/2003 | Ludvigsen ............ H04R 25/70 381/317 |
| 2006/0210090 | A1 | 9/2006 | Shennib |
| 2009/0052706 | A1 | 2/2009 | Gottschalk et al. |
| 2009/0116673 | A1 | 5/2009 | Heerlein et al. |
| 2010/0234757 | A1 | 9/2010 | Stromsted |
| 2011/0046511 | A1 | 2/2011 | Koo et al. |
| 2011/0142272 | A1 | 6/2011 | Takagi et al. |
| 2012/0029383 | A1 | 2/2012 | Henriksen et al. |
| 2013/0085411 | A1 | 4/2013 | Van |
| 2013/0102923 | A1 | 4/2013 | Cas et al. |
| 2013/0182855 | A1 | 7/2013 | Choi et al. |
| 2013/0251165 | A1 | 9/2013 | Jørgensen et al. |
| 2014/0270287 | A1 | 9/2014 | Park |
| 2015/0172837 | A1 * | 6/2015 | Martinez Azkorra . H04R 25/70 381/314 |
| 2015/0256942 | A1 | 9/2015 | Kinsbergen et al. |
| 2016/0057547 | A1 * | 2/2016 | Bürger ................ H04R 25/00 381/315 |
| 2017/0070833 | A1 | 3/2017 | Shennib |
| 2017/0230769 | A1 | 8/2017 | Nguyen et al. |
| 2017/0257713 | A1 * | 9/2017 | Westermann ......... H04W 12/06 |
| 2017/0286718 | A1 * | 10/2017 | Woss ................ G06F 16/9024 |
| 2017/0347205 | A1 * | 11/2017 | Aschoff ................ H04R 25/30 |
| 2018/0103328 | A1 | 4/2018 | Fitz |
| 2020/0389744 | A1 * | 12/2020 | Perscheid ............. H04R 25/70 |
| 2022/0201404 | A1 * | 6/2022 | Xu ....................... A61B 5/123 |

OTHER PUBLICATIONS

"International Preliminary Report on Patentability," for PCT Application No. PCT/US2020/046179 mailed Feb. 24, 2022 (16 pages).
"International Search Report and Written Opinion," for PCT Application No. PCT/US2020/046179 mailed Feb. 1, 2021 (23 pages).
"Invitation to Pay Additional Fees," for PCT Application No. PCT/US2020/046179 mailed Nov. 25, 2020 (20 pages).
"Mr. Bianco's Kindergarten Classroom—44 Sounds in the English Language," https://school.judsonisd.org/webpages/cbianco/readinghelp.cfm?subpage=23888, Oct. 13, 2014 (3 pages).
"Report of the Informal Working Group on Prevention of deafness and Hearing Impairment Programme Planning," World Health Organization Report, Geneva, Jun. 18-21, 1991 (24 pages).
AARP "Consumer Guide to Managing Hearing Loss," AARP 2010 (24 pages).
Aldaz, Gabriel, et al. "Smartphone-Based System for Learning and Inferring Hearing Aid Settings," J. Am. Acad. Audiol. Oct. 2016; 27(9): 732-749 (37 pages).
Carhart, Raymond "Selection of Hearing Aids," Archives of Otolaryngology 1946 44(1): 1-18 (18 pages).
Cox, Robyn M. "A Structured Approach to Hearing Aid Selection," Ear and Hearing 1985, vol. 6, No. 5 pp. 226-239 (14 pages).
Cox, Robyn M., et al. "The Contour Test of Loudness Perception," Ear and Hearing: vol. 18(5) Oct. 1997 pp. 388-400 (13 pages).
Hawkins, David B. "A Historical Perspective on Hearing Aid Selection," The Hearing Review, Nov./Dec. 1994, pp. 9-12 (4 pages).
Kuk, Francis, et al. "MPO: A Forgotten Parameter in Hearing Aid Fitting," he Hearing Review, https://www.hearingreview.com/practice-building/practice-management/mpo-a-forgotten-parameter-in-hearing-aid-fitting, Jun. 4, 2008 (20 pages).
Nance, Georgie, et al. "Hearing-Aid Evaluation: An Examination of Two Procedures," Bulletin of Prosthetics Research—Spring 1968 pp. 119-124 (6 pages).
Palmer, Catherine V., et al. "Overview and Rationale for Prescriptive Formulas for Linear and Nonlinear Hearing Aids," Chapter 1 of Strategies for Selecting and Verifying Hearing Aid Fittings Second Edition (1996) edited by Michael Valente (22 pages).
Recker, Karrie, et al. "Comparison of Adaptive Versions of the CCT and NST," Starkey Hearing Technologies Research Poster, 2012, available at URL <https://order.starkeypro.com/pdfs/research-briefs/Comparison_of_Adaptive_Versions_of_the_CCT_and_NST.pdf> (1 page).
Tecca, John E., et al. "The Application of an Adaptive Procedure to the California Consonant Test for Hearing Aid Evaluation," Ear and Hearing 1982, vol. 3, No. 2, pp. 72-76 (5 pages).

\* cited by examiner

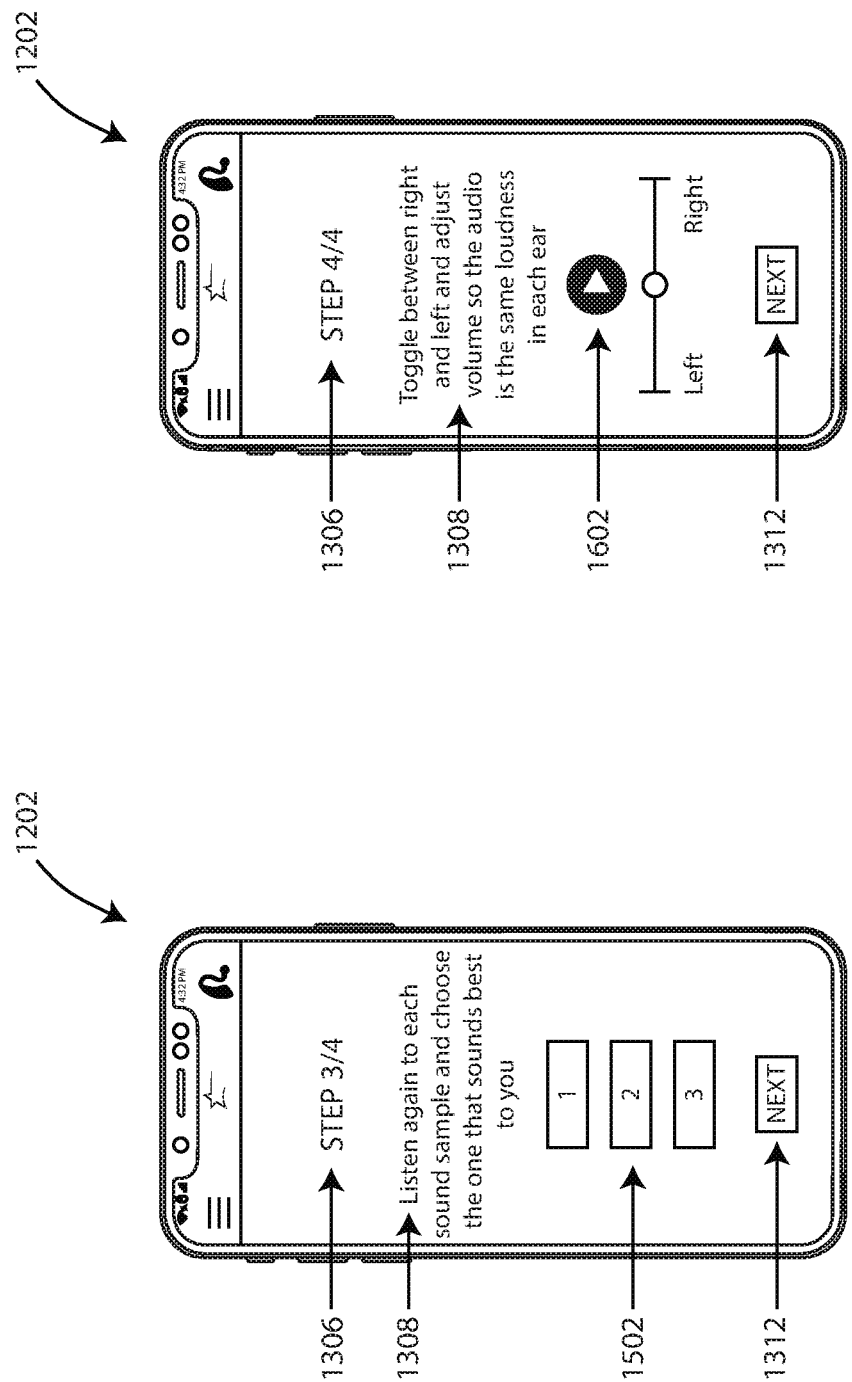

SYSTEMS, DEVICES AND METHODS FOR FITTING HEARING ASSISTANCE DEVICES

This application is being filed as a PCT International Patent application on Aug. 13, 2020, in the name of Starkey Laboratories, Inc., a U.S. national corporation, applicant for the designation of all countries, and William F. Austin, a U.S. Citizen, and David Alan Fabry, a U.S. Citizen, and Justin R. Burwinkel, a U.S. Citizen, and Jeffrey Paul Solum, a U.S. Citizen, and Chris Howes, a U.S. Citizen, and Manfred Stoifl, a Citizen of Singapore, and claims priority to U.S. Provisional Patent Application No. 62/887,331 filed Aug. 15, 2019, the contents of which are herein incorporated by reference in its entirety.

FIELD

Embodiments herein relate to systems, devices and methods for fitting hearing assistance devices.

BACKGROUND

Hearing assistance devices can provide tremendous benefit to those with some degree of hearing loss or perceived hearing difficulty. Modern hearing assistance devices are extremely powerful and have many capabilities. However, each device needs to be configured properly for the device wearer to achieve maximum benefit. This process can be referred to as "fitting" of the hearing assistance device. Typically, the fitting process is performed by a professional such as an audiologist.

SUMMARY

Embodiments herein relate to systems, devices and methods for fitting hearing assistance devices. In a first aspect, a method of fitting a hearing assistance device is included, the method including providing an audio sample to a hearing assistance device wearer, receiving input from the hearing assistance device wearer regarding a preferred sound volume or perceived loudness, receiving input from the hearing assistance device wearer with the external device regarding a bass/treble balance, and determining a maximum power output of the hearing assistance device that does not exceed a loudness discomfort level (LDL).

In a second aspect, in addition to one or more of the preceding or following aspects, or in the alternative to some aspects, a method can include receiving input from the hearing assistance device wearer regarding a binaural balance.

In a third aspect, in addition to one or more of the preceding or following aspects, or in the alternative to some aspects, a method can further include receiving input from the hearing assistance device wearer using an external device and sending programming data from the external device to the hearing assistance device based on the received input.

In a fourth aspect, in addition to one or more of the preceding or following aspects, or in the alternative to some aspects, the programming data can include device setting values, wherein an external device converts received input from the hearing assistance device wearer and the determined maximum power output into the device setting values, and the device setting values are specific to the type of hearing assistance device.

In a fifth aspect, in addition to one or more of the preceding or following aspects, or in the alternative to some aspects, a method can further include sending data from the external device across a data network to a server in a remote location, the data based on the received input from the hearing assistance device wearer and the determined maximum power output.

In a sixth aspect, in addition to one or more of the preceding or following aspects, or in the alternative to some aspects, a method can further include sending device settings from the remote location back to the hearing assistance device, wherein the device settings are determined based on the received input from the hearing assistance device wearer and the determined maximum power output.

In a seventh aspect, in addition to one or more of the preceding or following aspects, or in the alternative to some aspects, an external device used with systems and methods herein includes a speaker.

In an eighth aspect, in addition to one or more of the preceding or following aspects, or in the alternative to some aspects, an external device used with systems and methods herein includes a microphone, a speaker and a display screen.

In a ninth aspect, in addition to one or more of the preceding or following aspects, or in the alternative to some aspects, an external device can be a smartphone.

In a tenth aspect, in addition to one or more of the preceding or following aspects, or in the alternative to some aspects, receiving input from the hearing assistance device wearer with the external device regarding a bass/treble balance includes presenting the hearing assistance device wearer with a first plurality of preselected bass/treble balance settings and receiving input from the hearing assistance device wearer regarding preference.

In an eleventh aspect, in addition to one or more of the preceding or following aspects, or in the alternative to some aspects, a method can further include presenting the hearing assistance device wearer with a second plurality of preselected bass/treble balance settings based on received preference input.

In a twelfth aspect, in addition to one or more of the preceding or following aspects, or in the alternative to some aspects, receiving input from the hearing assistance device wearer regarding a binaural balance can include presenting the hearing assistance device wearer with a first plurality of preselected binaural balance settings and receiving input from the hearing assistance device wearer regarding which one they prefer.

In a thirteenth aspect, in addition to one or more of the preceding or following aspects, or in the alternative to some aspects, a method can further include presenting the hearing assistance device wearer with a second plurality of preselected binaural balance settings based on received input from the hearing assistance device wearer regarding which one they prefer.

In a fourteenth aspect, in addition to one or more of the preceding or following aspects, or in the alternative to some aspects, a hearing assistance device can be a hearing aid under 21 C.F.R. § 801.420 or similar regulations.

In a fifteenth aspect, in addition to one or more of the preceding or following aspects, or in the alternative to some aspects, an operation of receiving input from the hearing assistance device wearer with the external device regarding a bass/treble balance occurs after an operation of receiving input from the hearing assistance device wearer with the external device regarding a preferred sound volume or perceived loudness.

In a sixteenth aspect, in addition to one or more of the preceding or following aspects, or in the alternative to some aspects, an operation of receiving input from the hearing assistance device wearer with the external device regarding a bass/treble balance occurs before the operation of receiving input from the hearing assistance device wearer with the external device regarding a preferred sound volume or perceived loudness.

In a seventeenth aspect, in addition to one or more of the preceding or following aspects, or in the alternative to some aspects, an operation of receiving input from the hearing assistance device wearer with the external device regarding a binaural balance occurs after the operation of determining a maximum power output of the hearing assistance device that does not exceed a loudness discomfort level.

In an eighteenth aspect, in addition to one or more of the preceding or following aspects, or in the alternative to some aspects, an operation of receiving input from the hearing assistance device wearer with an external device regarding a binaural balance occurs before the operation of determining a maximum power output of the hearing assistance device that does not exceed a loudness discomfort level.

In a nineteenth aspect, in addition to one or more of the preceding or following aspects, or in the alternative to some aspects, an operation of providing an audio sample to a hearing assistance device wearer includes at least one of: wirelessly streaming the audio sample to the hearing assistance device, accessing data stored on the hearing assistance device representing the audio sample, playing the audio sample through a speaker of an external device, and prompting an individual to generate the audio sample.

In a twentieth aspect, in addition to one or more of the preceding or following aspects, or in the alternative to some aspects, wirelessly streaming the audio sample to the hearing assistance device further includes playing the audio sample through a speaker forming part of the hearing assistance device.

In a twenty-first aspect, in addition to one or more of the preceding or following aspects, or in the alternative to some aspects, prompting an individual to generate the audio sample further includes monitoring the sounds generated by the individual for sound volume.

In a twenty-second aspect, in addition to one or more of the preceding or following aspects, or in the alternative to some aspects, prompting an individual to generate the audio sample includes providing specific instructions for generating sound.

In a twenty-third aspect, in addition to one or more of the preceding or following aspects, or in the alternative to some aspects, prompting an individual to generate the audio sample includes providing a script for the individual to follow or mimic.

In a twenty-fourth aspect, in addition to one or more of the preceding or following aspects, or in the alternative to some aspects, prompting an individual to generate the audio sample includes prompting the device wearer to generate sounds to ensure that the wearer is comfortable with his or her own voice.

In a twenty-fifth aspect, in addition to one or more of the preceding or following aspects, or in the alternative to some aspects, the operation of providing an audio sample to a hearing assistance device wearer includes both streaming the audio sample to the hearing assistance device and playing the audio sample through the speakers of an external device.

In a twenty-sixth aspect, in addition to one or more of the preceding or following aspects, or in the alternative to some aspects, a method can further include qualifying the device wearer based on the severity of their hearing impairment or based on a perceived hearing handicap.

In a twenty-seventh aspect, in addition to one or more of the preceding or following aspects, or in the alternative to some aspects, qualifying the device wearer can include verifying that the device wearer has a hearing loss that is less than profound.

In a twenty-eighth aspect, in addition to one or more of the preceding or following aspects, or in the alternative to some aspects, qualifying the device wearer can include verifying that the device wearer has a hearing loss that is less than severe.

In a twenty-ninth aspect, in addition to one or more of the preceding or following aspects, or in the alternative to some aspects, qualifying the device wearer can include presenting the device wearer with a panel of queries directed to the severity of their hearing impairment or their perceived hearing handicap and receiving feedback from the device wearer regarding the same.

In a thirtieth aspect, in addition to one or more of the preceding or following aspects, or in the alternative to some aspects, a method can further include estimating the severity of their hearing impairment or their perceived hearing handicap based on the device wearer's feedback.

In a thirty-first aspect, in addition to one or more of the preceding or following aspects, or in the alternative to some aspects, presenting the device wearer with a panel of queries directed to the severity of their hearing impairment or their perceived hearing handicap can be performed prior to providing an audio sample to a hearing assistance device wearer.

In a thirty-second aspect, in addition to one or more of the preceding or following aspects, or in the alternative to some aspects, qualifying the device wearer can include presenting the device wearer with a series of audio samples and questions regarding content of the same.

In a thirty-third aspect, in addition to one or more of the preceding or following aspects, or in the alternative to some aspects, a series of audio samples can include at least one of a phoneme confusion test, a California Consonant Test, a Chear Auditory Perception test, and a speech-in-noise test.

In a thirty-fourth aspect, in addition to one or more of the preceding or following aspects, or in the alternative to some aspects, a series of audio samples and questions regarding content of the same can be administered as part of a game.

In a thirty-fifth aspect, in addition to one or more of the preceding or following aspects, or in the alternative to some aspects, a method can further include qualifying the device wearer based on settings for a previous device configured for the device wearer.

In a thirty-sixth aspect, in addition to one or more of the preceding or following aspects, or in the alternative to some aspects, a method can further include qualifying a sound field in which the device wearer is present.

In a thirty-seventh aspect, in addition to one or more of the preceding or following aspects, or in the alternative to some aspects, qualifying the sound field includes evaluating at least one of evaluating echoes, reverberation time, decay time, critical distance, room impulse measure, absorption coefficient across a human detectable frequency band, ambient noise, comb filter distortion, coloration distortion, early reflection, and late reflection.

In a thirty-eighth aspect, in addition to one or more of the preceding or following aspects, or in the alternative to some aspects, qualifying the sound field includes emitting a sample sound and evaluating sound received at the hearing assistance device.

In a thirty-ninth aspect, in addition to one or more of the preceding or following aspects, or in the alternative to some aspects, a sample sound can be emitted from an external device.

In a fortieth aspect, in addition to one or more of the preceding or following aspects, or in the alternative to some aspects, evaluating sound received at the hearing assistance device includes comparing the sample sound with the sound received across a human detectable frequency band.

In a forty-first aspect, in addition to one or more of the preceding or following aspects, or in the alternative to some aspects, the audio sample provided to the hearing assistance device wearer can be manipulated based on acoustic properties of the sound field in which the hearing assistance device wearer is located.

In a forty-second aspect, in addition to one or more of the preceding or following aspects, or in the alternative to some aspects, manipulations of an audio sample can include changing a delay in the audio sample.

In a forty-third aspect, in addition to one or more of the preceding or following aspects, or in the alternative to some aspects, a method can further include presenting the device wearer with a series of audio samples and questions regarding content of the same; and receiving answers to the questions from the device wearer.

In a forty-fourth aspect, in addition to one or more of the preceding or following aspects, or in the alternative to some aspects, a method can further include calculating an accuracy score based the received answers and initiating a corrective measure if the accuracy score crosses a threshold value.

In a forty-fifth aspect, in addition to one or more of the preceding or following aspects, or in the alternative to some aspects, a corrective measure can include notifying the device wearer that they should contact a care provider and terminating the fitting procedure.

In a forty-sixth aspect, in addition to one or more of the preceding or following aspects, or in the alternative to some aspects, a method can further include recording speech from the device wearer and evaluating the recorded speech to classify the degree or configuration of hearing loss of the device wearer.

In a forty-seventh aspect, in addition to one or more of the preceding or following aspects, or in the alternative to some aspects, a method can further include requesting the device wearer to speak a plurality of words prior to the operation of recording speech from the device wearer.

In a forty-eighth aspect, in addition to one or more of the preceding or following aspects, or in the alternative to some aspects, a method can further include determining a location of the device wearer, evaluating regulations for device fitting based on the location, and terminating or modifying the fitting procedure or notifying the device wearer that they should contact a care provider based on the regulation.

In a forty-ninth aspect, in addition to one or more of the preceding or following aspects, or in the alternative to some aspects, a method can further include reinitiating the operations of receiving input from the hearing assistance device wearer and determining a maximum power output of the hearing assistance device that does not exceed a loudness discomfort level (LDL) at a later time point.

In a fiftieth aspect, in addition to one or more of the preceding or following aspects, or in the alternative to some aspects, a later time point is at least 8 hours after the initial operations of receiving input from the hearing assistance device wearer and determining a maximum power output of the hearing assistance device.

In a fifty-first aspect, in addition to one or more of the preceding or following aspects, or in the alternative to some aspects, a method can further include reinitiating the operations of presenting the device wearer with a series of audio samples and questions regarding content of the same and receiving answers to the questions from the device wearer at a later time point.

In a fifty-second aspect, in addition to one or more of the preceding or following aspects, or in the alternative to some aspects, a method can further include reinitiating the operations of recording speech from the device wearer and evaluating the recorded speech to classify the degree or configuration of hearing loss of the device wearer at a later time point.

In a fifty-third aspect, in addition to one or more of the preceding or following aspects, or in the alternative to some aspects, a method can further include activating a frequency lowering/shifting algorithm on the hearing assistance device if a test result based on "s" and "sh" phonemes crosses a threshold value. It will be appreciated that in some languages (such as tonal languages) these particular examples may not be speech sounds, but a similar principal could still be applied and/or in various embodiments other phonemes can be tested for confusion.

In a fifty-fourth aspect, in addition to one or more of the preceding or following aspects, or in the alternative to some aspects, a method can further include activating a frequency lowering/shifting algorithm on the hearing assistance device if a test result based on "s" and "sh" phonemes crosses a threshold value and high-frequency gain values on the hearing assistance device are maxed out or otherwise should not be increased. It will be appreciated that in some languages (such as tonal languages) these particular examples may not be speech sounds, but a similar principal could still be applied and/or in various embodiments other phonemes can be tested for confusion.

In a fifty-fifth aspect, a hearing assistance device fitting system is included having a hearing assistance device that can include a control circuit, a microphone in electrical communication with the control circuit, an electroacoustic transducer for generating sound in electrical communication with the control circuit, a power supply circuit in electrical communication with the control circuit, and an external device in wireless communication with the hearing assistance device. The system can be configured to provide an audio sample to a hearing assistance device wearer, receive input from the hearing assistance device wearer, receive input from the hearing assistance device wearer regarding a bass/treble balance, and determine a maximum power output of the hearing assistance device that does not exceed a loudness discomfort level (LDL).

In a fifty-sixth aspect, in addition to one or more of the preceding or following aspects, or in the alternative to some aspects, a system can further be configured to receive input from the hearing assistance device wearer with the external device regarding a binaural balance.

In a fifty-seventh aspect, in addition to one or more of the preceding or following aspects, or in the alternative to some aspects, a system can further be configured to send programming data from the external device to the hearing assistance device based on the received input from the hearing assistance device wearer and the determined maximum power output.

In a fifty-eighth aspect, in addition to one or more of the preceding or following aspects, or in the alternative to some aspects, the programming data can include device setting values, wherein the device setting values are specific to the type of hearing assistance device, wherein the external device converts the received input from the hearing assistance device wearer and the determined maximum power output into the device setting values.

In a fifty-ninth aspect, in addition to one or more of the preceding or following aspects, or in the alternative to some aspects, a system can further be configured to send programming data from the external device across a data network to a server in a remote location, the programming data based on the received input from the hearing assistance device wearer and the determined maximum power output.

In a sixtieth aspect, in addition to one or more of the preceding or following aspects, or in the alternative to some aspects, a system can further be configured to send device settings from the remote location back to the hearing assistance device, wherein the device settings are determined based on the received input from the hearing assistance device wearer and the determined maximum power output.

In a sixty-first aspect, in addition to one or more of the preceding or following aspects, or in the alternative to some aspects, an external device includes a speaker.

In a sixty-second aspect, in addition to one or more of the preceding or following aspects, or in the alternative to some aspects, an external device includes a microphone, a speaker and a display screen.

In a sixty-third aspect, in addition to one or more of the preceding or following aspects, or in the alternative to some aspects, an external device is a smartphone or a tablet device.

In a sixty-fourth aspect, in addition to one or more of the preceding or following aspects, or in the alternative to some aspects, the system can further be configured to store component configuration data.

In a sixty-fifth aspect, in addition to one or more of the preceding or following aspects, or in the alternative to some aspects, the system can further be configured to automatically detect the type of receiver and/or cable attached to the hearing assistance device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 15 is a schematic view of an external device in accordance with various embodiments herein.

FIG. 16 is a schematic view of an external device in accordance with various embodiments herein.

Figure 1:
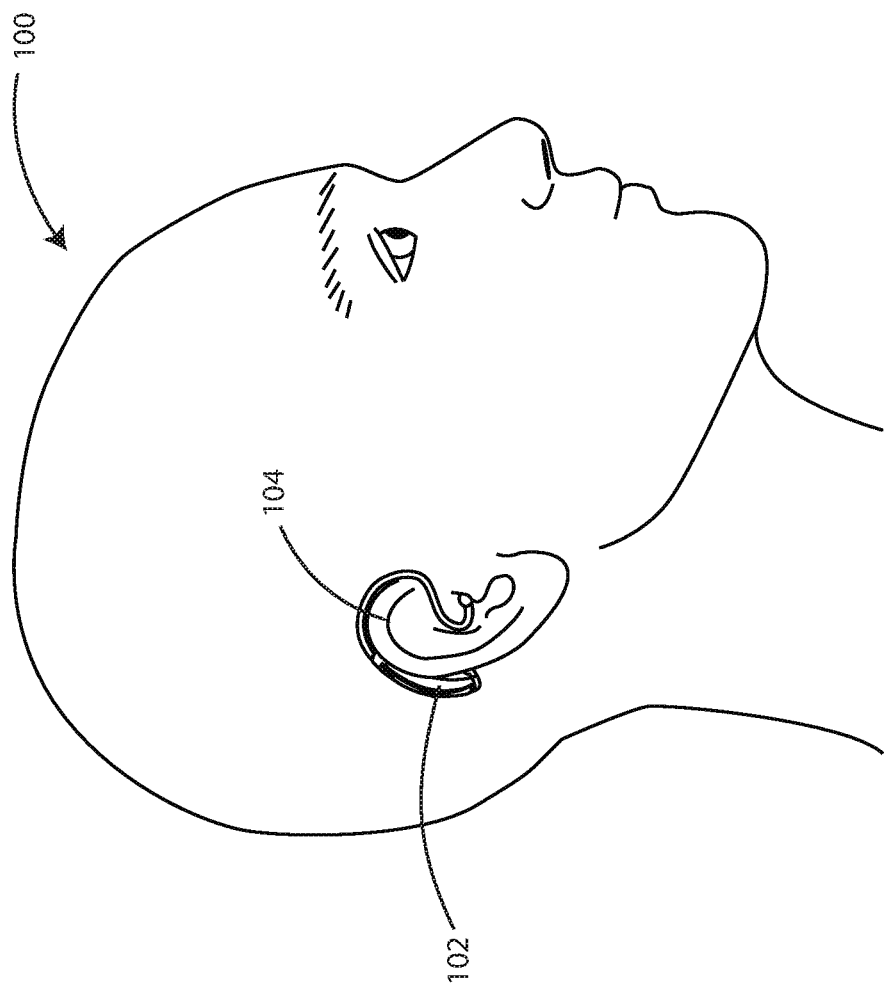
FIG. 1 is a schematic view of a device user in accordance with various embodiments herein.

While embodiments are susceptible to various modifications and alternative forms, specifics thereof have been shown by way of example and drawings and will further be described in detail. It should be understood, however, that the scope herein is not limited to the particular aspects described. On the contrary, the intention is to cover modifications, equivalents, and alternatives falling within the spirit and scope herein.

DETAILED DESCRIPTION

As described above, hearing assistance devices typically need to be configured properly for the device wearer to achieve maximum benefit. This process can be referred to as "fitting" of the hearing assistance device. Previously, fitting processes have been performed by professionals, such as an audiologist or qualified professional. However, that creates less flexibility for the device wearer in terms of how they can obtain their device and get it setup for use. Qualified professionals, including but not limited to audiologists, may also be limited in terms of the number of patients that they are able to access or assist with direct supervision due to potential geographical limitations, time constrains, language barriers, and the like.

Allowing the device wearer (or another person who is not a qualified professional regarding hearing assistance devices such as a caretaker of the device wearer or legal guardian thereof) to execute a fitting process can increase flexibility for purchase and setup. However, the nature of a typical fitting process is not conducive for execution by a lay person. In some cases, the concepts associated with various settings and their parameters may be difficult for the lay person to grasp. Also, it has been discovered that some lay people may attempt to perform the fitting procedure in a complex sound environment that may not be conducive to properly executing a fitting procedure.

However, embodiments herein relate to systems, devices and methods for fitting hearing assistance devices to allow for fitting to be executed without the assistance of or direct supervision from a hearing professional in some circumstances. In specific, embodiments herein include advanced procedures and devices that can automate or partially automate the fitting process. Embodiments herein can include systems and devices that can perform various functions including evaluating or qualifying the sound environment where the device wearer is located to ensure that it is sufficient to proceed with a proper fitting procedure.

In addition, some potential device wearers may have a hearing loss that is so substantial, debilitating, or otherwise complicated in nature that they are not a good candidate for working with a device to perform a fitting in the absence of a hearing professional. Some potential device wearers may have physical, emotional, neurological or cognitive limitations which could prevent them from being a good candidate to perform a fitting in the absence of a hearing professional. As such, some embodiments herein can also include systems and devices that can evaluate or qualify the hearing status and candidacy of the device wearer (e.g., detect the degree and/or nature of hearing loss and perceived hearing impairment). In some cases, prior experience with a hearing assistance device may contribute to the candidacy criteria for fittings performed in the absence of a hearing professional. In some municipalities, there may be specific laws, regulations, or guidance that may specify the candidacy criteria for fittings performed in the absence of a hearing professional. For example, it may be determined that device wearers under the age of 18 may be legally prohibited from using hearing devices that are fit in the absence of a licensed audiologist, which is a type of hearing professional with a specific qualification and/or credential for, e.g., the diagnosis and management of pediatric communication disorders. Qualifying the hearing status/candidacy of the device wearer may help to ensure that it is appropriate for the device wearer to proceed with an automated or partially automated fitting procedure or if it is appropriate for the device wearer to proceeded with a fitting in the absence of a hearing professional.

Figure 2:
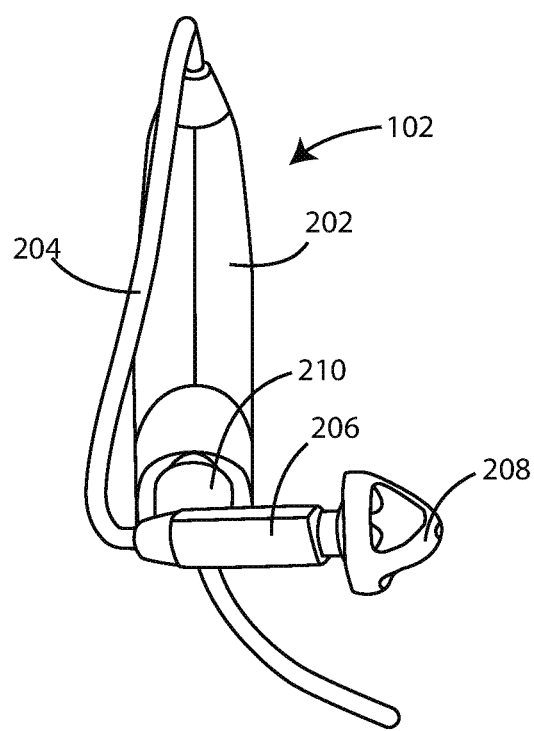
FIG. 2 is a schematic view of a hearing assistance device in accordance with various embodiments herein.

Referring now to FIG. 1, a schematic view is shown of a device wearer 100 in accordance with various embodiments herein. The device wearer 100 is wearing a hearing assistance device 102 on or about their ear 104. Referring now to FIG. 2, a schematic view is shown of a hearing assistance device 102 in accordance with various embodiments herein. The hearing assistance device 102 can include a device housing 202. The device housing 202 can define a battery compartment 210 into which a battery can be disposed to provide power to the device. The hearing assistance device 102 can also include a receiver 206 adjacent to an earbud 208. The receiver 206 can include a component that converts electrical impulses into sound, such as an electroacoustic transducer, speaker, or loud speaker. A cable 204 or connecting wire can include one or more electrical conductors and provide electrical communication between components inside of the device housing 202 and components inside of the receiver 206.

Figure 3:
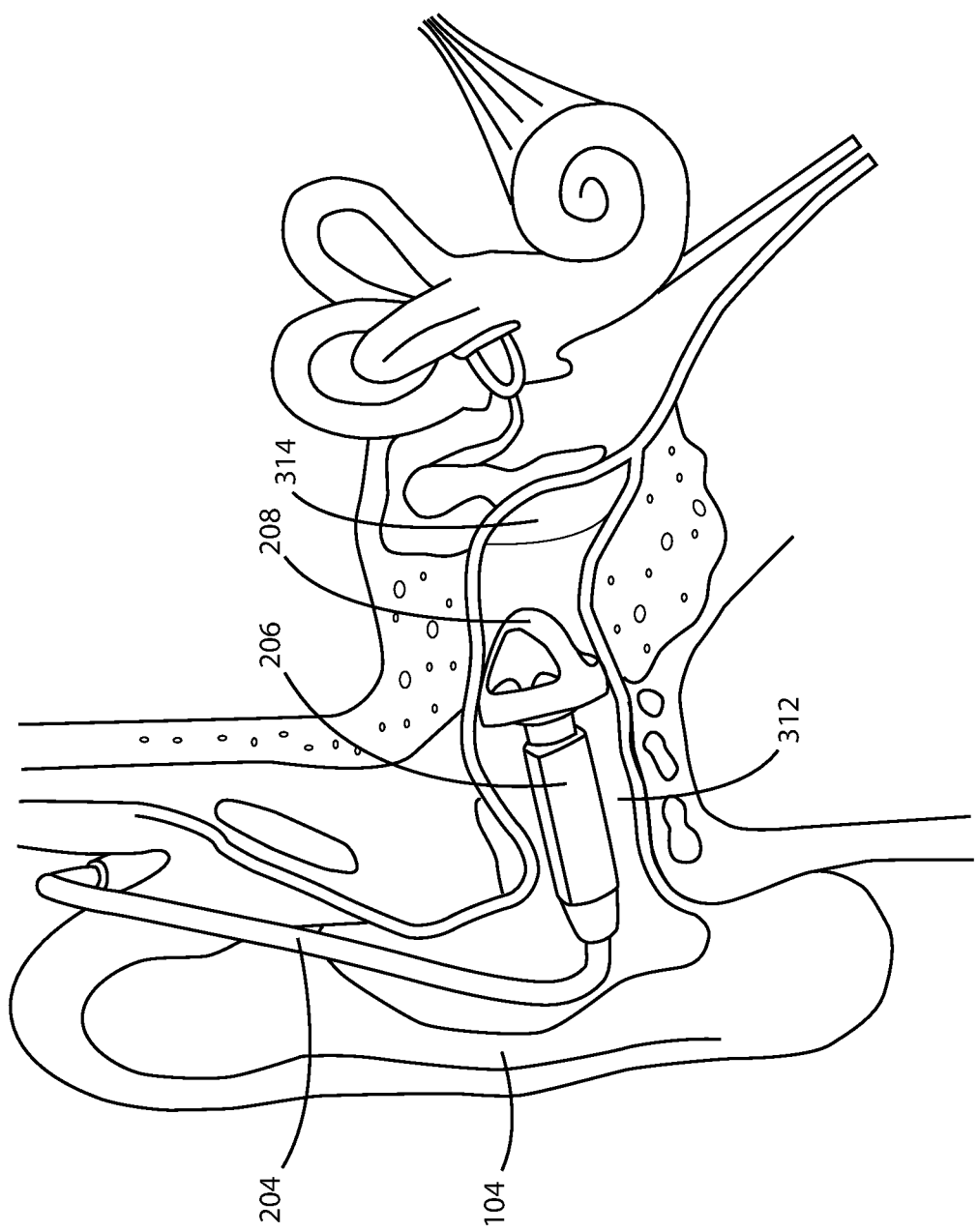
FIG. 3 is a schematic view of a hearing assistance device disposed within the ear canal in accordance with various embodiments herein.

Referring now to FIG. 3, a schematic view is shown of a hearing assistance device disposed within the ear canal in accordance with various embodiments herein. In this view, the receiver 206 and the earbud 208 are both within the ear canal 312, but do not directly contact the tympanic membrane 314. The device housing is mostly obscured in this view behind the pinna 310, but it can be seen that the cable 204 passes over the top of the pinna 310 and down to the entrance to the ear canal 312.

Figure 4:
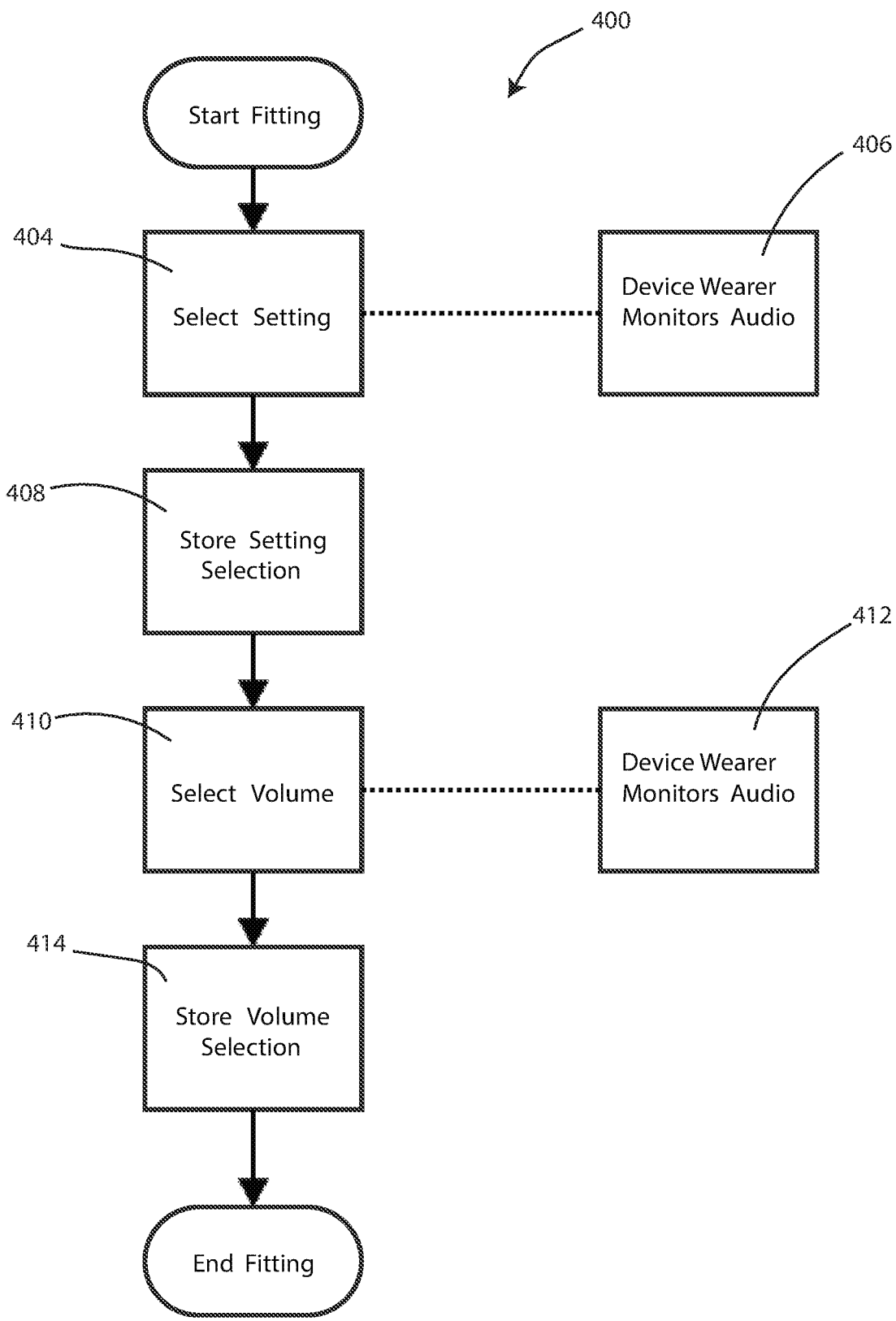
FIG. 4 is a flow chart of a method of fitting a hearing assistance device in accordance with various embodiments herein.

Referring now to FIG. 4, a flow chart is shown of a method 400 of fitting a hearing assistance device in accordance with various embodiments herein. A first operation can include providing and/or playing one or more audio samples and then prompting 404 the device wearer to select a device setting value, which can indicate which audio sample they prefer. The device wearer can be prompted visually, audibly, and/or tactilely. It will be appreciated that any audio samples can be presented in an "A" vs. "B" format for the device wearer to select the preferred sound, with, in some cases, "A" being substantially different than "B" and gradually narrowing down the differences with successive presentations of an "A" and a "B" until the device wearer no longer perceives a difference.

In some embodiments, providing an audio sample or instructions to a device wearer can include at least one of streaming the audio sample or instructions to the hearing assistance device (streaming wirelessly, through wired connectivity, or through a combination of wired and wireless connectivity), accessing data stored in memory on the hearing assistance device representing the audio sample or instructions, playing the audio sample or instructions through a speaker of an external device, and/or prompting one or more of the device wearer and an individual other than the device wearer to generate the audio sample. In some embodiments, more than one way of providing the audio sample can be used.

Streaming the audio sample and/or instructions to the hearing assistance device can further include playing the audio sample or instructions through a speaker forming part of the hearing assistance device.

In some embodiments, prompting one or more of the device wearer and an individual other than the device wearer to generate the audio sample further includes monitoring the sounds generated by the individual for sound volume. In some embodiments, prompting an individual to generate the audio sample includes providing specific instructions for generating sound. In some embodiments, prompting an individual to generate the audio sample includes providing a script for the individual to follow or mimic. In some embodiments, prompting an individual to generate the audio sample includes prompting the device wearer to generate sounds to ensure that the wearer is comfortable with his or her own voice.

In some embodiments, providing an audio sample to a hearing assistance device wearer includes both streaming the audio sample to the hearing assistance device and playing the audio sample through the speakers of an external device. In some embodiments, a delay value is determined for one or more speakers and the production of at least one audio sample is set to appropriately synchronize the streaming of an audio sample to the hearing assistance device and the playing of an audio sample through the speakers of an external device. In some embodiments, a delay value may be communicated between the hearing device and one or more operatively connected devices or speakers.

The device setting can be for various specific items. By way of example, the setting can include, but is not limited to, one or more of amplification (gain) values at one or more frequencies (which can include bass/treble balance), microphone directionality algorithms and patterns, compression thresholds, speeds and knee points or ratios at one or more frequencies, delay settings at one or more frequencies, frequency shifting algorithms, noise reduction algorithms, speech enhancement algorithms, speech or tonal indictor volumes, and the like. In some embodiments, settings can specifically be related to amplification (gain) values centered around frequencies corresponding to production of various speech sounds (see, e.g., TABLE 1 below). Testing speech sounds (e.g., Ling speech sounds, and the like) may include periodically not making a sound and then seeing if a false-positive is reported from the listener. Thus, it is also understood that a period (milliseconds to seconds) of relative silence may constitute a speech sound. After selecting the setting value, then a second operation can include the device wearer monitoring 406 audio sample(s) of a duration sufficient to determine the appropriateness of the setting value. The audio sample(s) can be provided in various ways. In some embodiments, the audio sample(s) can be streamed to the hearing assistance device from a separate device, such as a smartphone, a tablet, an audio streamer device, or the like (which could be conveyed through BLUETOOTH audio streaming or another technique). In some embodiments, the audio sample(s) may be played through an induction loop, proximate to the wearer of the device, from which the hearing assistance device can receive the audio sample(s) signal through a telecoil or magnetic sensor. In some embodiments, the audio samples may be played through an intermediary device or hearing device accessory, such as a media streamer, companion microphone device, neckloop, and the like. In some embodiments, a sound emitting device in the vicinity of the device wearer can be controlled to emit audio sample(s) through the air. For example, a type of device with a speaker can be used to emit audio sample(s). In some embodiments, one or more of the device wearer and another person can be prompted to speak or otherwise create noise for the audio sample(s).

In a third operation, the setting selection can be stored 408 in one or more devices. For example, the setting selection can be stored in the memory of the hearing assistance device. In some embodiments, the setting selection can be stored in the memory of an accessory device to the hearing assistance device (e.g., companion microphone device, remote control, media streamer, smartphone, etc.). In some embodiments, the setting selection can be stored in the memory of a smartphone or tablet. In some embodiments, the setting selection can be relayed to a data network and then stored by a server in the cloud and/or by a server associated with the hearing assistance device manufacturer.

In a fourth operation, the device wearer can be prompted 410 to select a volume. The device wearer can be prompted visually, audibly, and/or tactilely.

A fitting process herein can also include adjustment of the maximum power output (MPO). In some scenarios, an MPO can be a maximum loudness setting. If the MPO is set too high, then the device wearer may experience aided loudness discomfort for high-level sounds. If the MPO is set too low, then there may not be adequate headroom or dynamic range. In some embodiments, the method can include determining a maximum power output of the hearing assistance device that does not exceed a loudness discomfort level (LDL). Then, a fifth operation can include the device wearer monitoring 412 audio sample(s) to determine the appropriateness of the volume setting. As before, the audio sample(s) can be provided in various ways.

In some embodiments, LDL may be determined by providing audio samples at various volumes (such as progressively increasing the volume) and receiving user feedback regarding their comfort to determine an LDL threshold value. In some embodiments, LDL and/or other assessments related to loudness herein can be determined by providing audio samples at three different volumes and receiving user feedback regarding their comfort to determine an LDL threshold value or other loudness-related setting, such as a gain value. In some embodiments, LDL may be determined or estimated by using a loudness contour test, such as that described by Cox and Alexander. See Cox, R M, Alexander, G C, Taylor, I M, and Gray, G A. "The Contour Test of loudness perception". Ear and Hearing, 18: 388-400 (1997). The Cox and Alexander loudness contour test provides seven loudness categories ranging from very soft to uncomfortable and maps the same for individuals against levels of warble tones (dB HL). In some embodiments, the uncomfortable category of the Cox and Alexander loudness contour test can be used to determine an LDL threshold value. However, various methods of determining LDL can be used herein. In some embodiments, the system can determine non-linear or abnormal loudness growth, such as recruitment. In some embodiments, the system can adapt hearing device settings based upon a determined non-linear or abnormal loudness growth of the user's volume perception in at least one ear.

Then, in a sixth operation, the setting selection can be stored 414 in the memory of one or more devices. In various embodiments, a value can be stored in the memory of one or more devices indicating that an initial fitting procedure has been completed.

It will be appreciated that some sound environments are complex and can distort sound as well as interfere with the intelligibility of sound. For example, aspects such as echoes, reverberation time, decay time, critical distance, room impulse, absorption coefficient across a human detectable frequency band, ambient noise, comb filter distortion, coloration distortion, early reflection, late reflection, noise generators, etc. can make a particular sound environment extremely complex. This is significant because the appropriateness of settings that may be selected by a device wearer may be adversely impacted by the sound environment they are in when the fitting procedure is performed.

Figure 5:
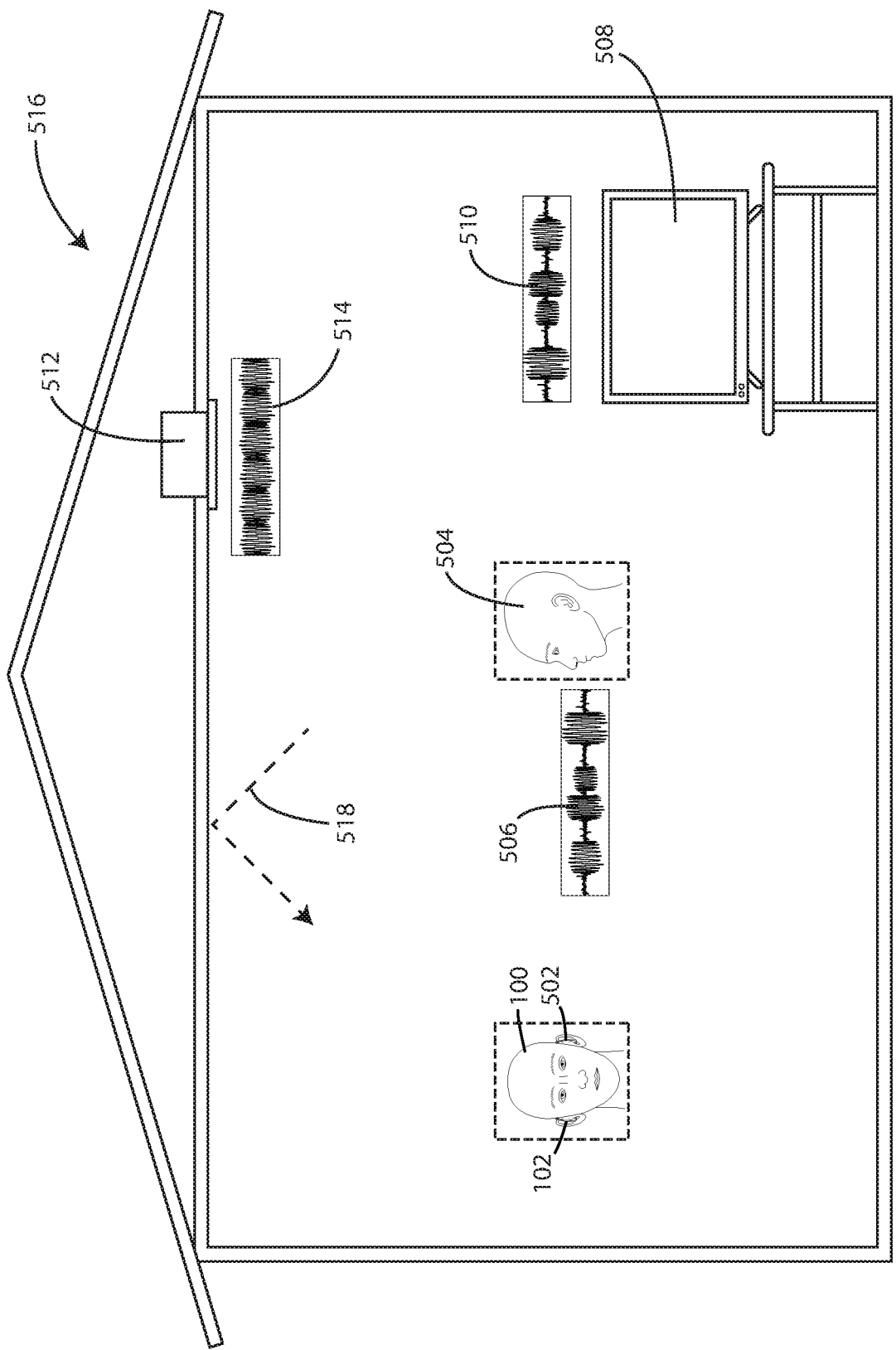
FIG. 5 is a schematic view of a sound environment in accordance with various embodiments herein.

Referring now to FIG. 5, a schematic view is shown of a sound environment 516 in accordance with various embodiments herein. A device wearer 100 is shown in the sound environment 516 wearing a first hearing assistance device 102 and a second hearing assistance device 502. The sound environment 516 can include multiple sound generators that may interfere with a fitting procedure. For example, the sound environment 516 may include another person 504 generating sound 506 that can interfere with audio sample(s) being provided to the device wearer. Further, various objects in the sound environment 516, such as a TV 508 (or other electronic device) can generate sound 510 that can interfere with audio sample(s) being provided to the device wearer. In some embodiments, equipment 512 (such as a fan, furnace, air conditioner, or the like) can generate sound 514 that can interfere with audio sample(s) being provided to the device wearer 100. In addition, the acoustics of the sound environment 516 can be less than ideal. For example, sound can reflect 518 off surfaces leading to echo, resonance, and reverberation amongst other sources of distortion that may adversely impact the ability of the device wearer to proceed properly with a fitting procedure.

Figure 6:
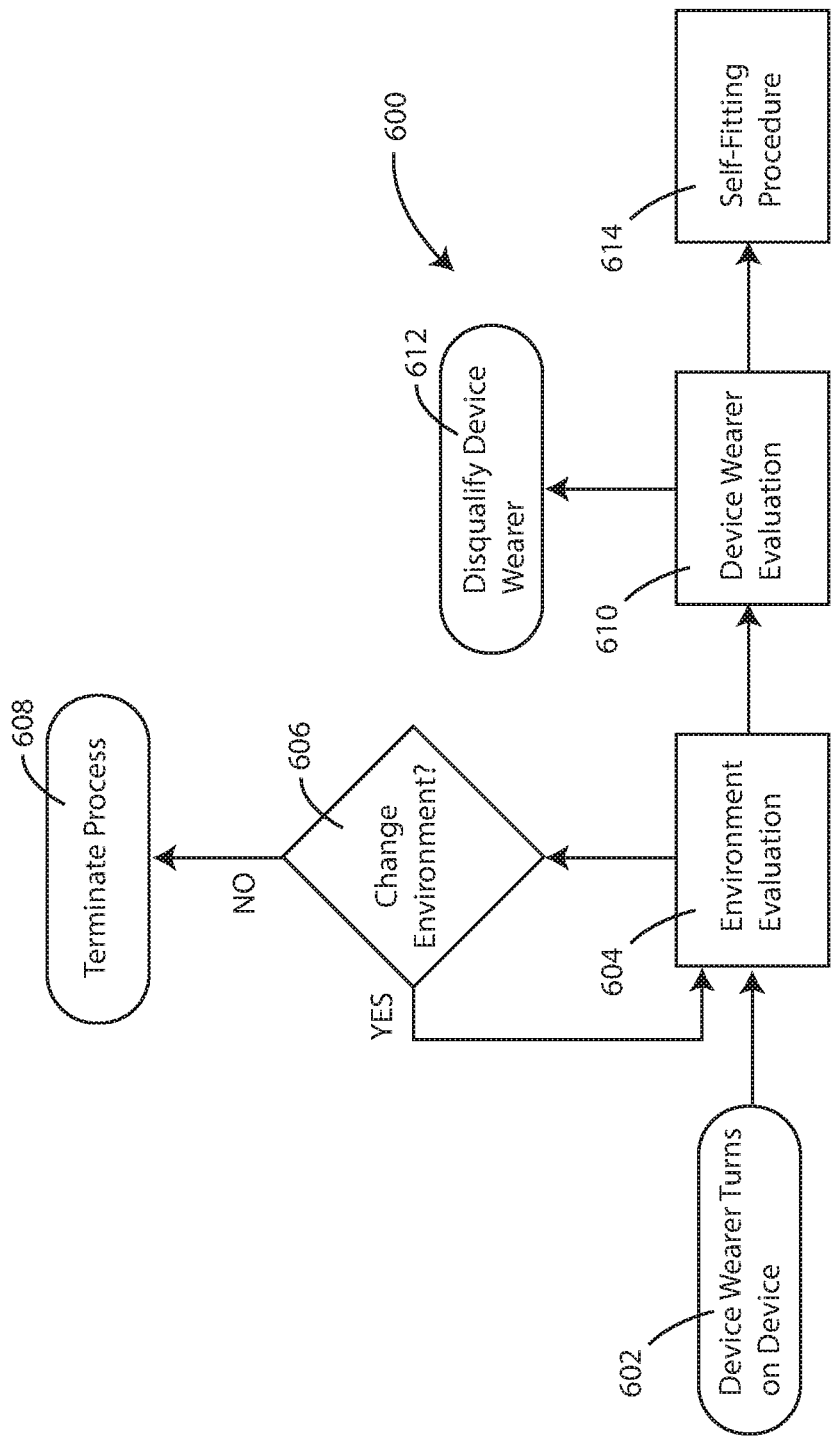
FIG. 6 is a flow chart of a method of fitting a hearing assistance device in accordance with various embodiments herein.

In some embodiments, a method of fitting a hearing assistance device can include operations related to environment qualification/evaluation. Referring now to FIG. 6, a flow chart is shown of a method 600 of fitting a hearing assistance device in accordance with various embodiments herein. In this method, a first operation can include the device wearer turning on 602 the hearing assistance device. In some embodiments, if the hearing assistance device has not been previously fitted (which can be determined by checking the value of a parameter stored in the memory of the hearing assistance device) then the hearing assistance device can automatically enter a fitting procedure mode. In some embodiments, the hearing assistance device can send a signal to a separate device (such as a smartphone or a hearing assistance device accessory) to trigger the initiation of a fitting procedure mode.

In another operation, the hearing assistance device or another device in communication therewith can perform an environment evaluation 604. Environment evaluation 604 can include qualifying the sound field in which the device wearer is present. In some embodiments, qualifying the sound field can include evaluating echoes, reverberation time, decay time, critical distance, room impulse measure, absorption coefficient across a human detectable frequency band, ambient noise, comb filter distortion, coloration distortion, early reflection, late reflection and the like. In some embodiments, qualifying the sound field can include emitting a sample sound and evaluating sound received at the hearing assistance device. In some embodiments, the sample sound is emitted from an external device. In some embodiments, evaluation of the acoustic environment of the device wearer can include evaluation of inputs derived from operatively connected acoustic sensors external to the hearing assistance device. In some embodiments, evaluating sound received at the hearing assistance device can include comparing the sample sound with the sound received across a human detectable frequency band. In some embodiments, the audio sample provided to the hearing assistance device wearer is manipulated based on acoustic properties of the sound field in which the hearing assistance device wearer is located. In some embodiments, the manipulation can include changing a delay in the audio sample or applying acoustic filters to the audio sample.

The environment evaluation 604 can include active and/or passive operations. As an example of an active operation, the environment evaluation 604 can include triggering a sound (generated by any device with a speaker or a person including the device wearer or a third party) and evaluating the signal generated by a microphone associated with the hearing assistance device. As an example of a passive operation, the environment evaluation can include using a microphone associated with the hearing assistance device to monitor for ambient sounds and aspects like echo (including echo time and/or echo magnitude) and reverberation in the sound environment.

If ambient sounds exceed an intensity threshold value, or the environment includes elements like echo, reverberation decay time, critical distance, room impulse measure, absorption coefficient across a human detectable frequency band, comb filter distortion, coloration distortion, early reflection, late reflection that exceeds a threshold value, or another parameter of the environment exceeds a threshold value, then the hearing assistance device itself can attempt to modify the acoustic environment of the device wearer. In some embodiments, the hearing assistance device may leverage mesh networks or the Internet of Things (IoT) to modify the environment 606 for the hearing assistance device fitting procedure. For example, the hearing assistance device may issue a command to a heating and cooling system to change, suspend, or even start (such as if testing a wind reduction algorithm) some operations during the fitting procedure. In some embodiments, the hearing assistance device wearer can be prompted to change the environment 606 in another operation. In some cases, such changes to the acoustic environment can be reversed after the fitting procedure ends (e.g., a command can be issued to a heating and cooling system to undue the changes previously made and/or the device wearer can be prompted to make such changes).

If the hearing assistance device controller or wearer can change the environment (e.g., turn off or otherwise quiet sound emitting devices in the environment and/or move to a different environment) then the method can return to the environment evaluation 604. However, if the hearing assistance device controller or wearer cannot change the environment, then the fitting process can be postponed or terminated 608.

Beyond the environment the device wearer is in, another aspect that is important for the fitting process is the inherent characteristics of the device wearer themselves. Not all individuals may be appropriate candidates for a fitting process to be performed by the device itself or without the direct supervision of a hearing professional. In some cases, some device wearers may be better candidates for working with a professional (such as an audiologist) to properly fit their device. As such, in another operation a device wearer evaluation 610 can be performed. The device wearer evaluation 610 can include various aspects including, but not limited to, assessing their hearing, testing their ability to follow instructions, administering self-assessment measures, collecting questionnaire data (e.g., case history information), evaluating settings for previous hearing assistance devices used by the device wearer, and the like.

In some embodiments, the evaluation 610 can include qualifying the device wearer based on the severity of their hearing impairment or perceived handicap. In some embodiments, qualifying the device wearer can include verifying that the device wearer has a hearing loss that is less than profound. In some embodiments, qualifying the device wearer comprises verifying that the device wearer has a hearing loss that is less than severe. As merely one example of hearing loss degrees associated with categories such as "profound" and "severe", the non-limiting classification scheme in Table 1 can be used.

TABLE 1

| Degree of Hearing Loss | Hearing Loss Range (dB HL) |
|---|---|
| Normal | −10 to 15 |
| Slight | 16 to 25 |
| Mild | 26 to 40 |
| Moderate | 41 to 55 |
| Moderately Severe | 56 to 70 |
| Severe | 71 to 90 |
| Profound | 91+ |

In some embodiments, qualifying the device wearer comprises presenting the device wearer with a panel of queries directed to the severity of their hearing impairment or hearing handicap and receiving feedback from the device wearer regarding the same. In some embodiments, the system can then estimate the severity of their hearing impairment based on the device wearer's feedback. In some embodiments, presenting the device wearer with a panel of queries directed to the severity of their hearing impairment or hearing handicap is performed prior to providing an audio sample to a hearing assistance device wearer. In some embodiments, qualifying the device wearer comprises presenting the device wearer with a series of audio samples and questions regarding content of the same. In some embodiments, the series of audio samples includes at least one of a phoneme confusion test, a California Consonant Test, and a Chear Auditory Perception test, or a speech-in-noise test. Speech-in-noise tests can include the QuickSIN (Quick Speech-in-noise Test) or HINT (Hearing in Noise Test), or the like. In some embodiments, the system can further calculate an accuracy score based on the received answers and initiate a corrective measure if the accuracy score crosses a threshold value. In some cases, the corrective measure can include notifying the device wearer that they should contact a care provider and terminating the fitting procedure. In some cases, accuracy scores on one or more tests can be used to provide a recommendation to the device wearer regarding accessory devices that might be useful to them, such as a remote microphone device.

In some embodiments, the series of audio samples and questions regarding content of the same are administered as part of a game.

Individuals with specific degrees or types of hearing loss can exhibit characteristic speech patterns. In some embodiments, the evaluation can include recording speech from the device wearer and evaluating the recorded speech to classify the degree or configuration of hearing loss of the device wearer. In some embodiments, a method can include requesting the device wearer to speak a plurality of words prior to the operation of recording speech from the device wearer.

In some cases, the device wearer evaluation 610 can include presenting the device wearer with a panel of queries directed to the severity of their hearing impairment, their perceived hearing handicap, and/or their specific listening needs.

It will be appreciated that the severity of possible hearing impairment of an individual may differ from the individual's perceived level of hearing handicap. These types of incongruencies can result from the individual's unique experiences, self-image, emotions, perceptions, and the like. It will be appreciated that, in various embodiments, determining a degree of hearing impairment and a perceived level of hearing handicap may be used by the hearing device system either in isolation or in combination. It will be further appreciated that, in various embodiments, a specific determination of either a degree of hearing impairment or a perceived level of hearing handicap may be prescribed (i.e., required) or preferred. In one illustrative example, an individual can be discouraged or prevented from proceeding with an automated or partially automated hearing device fitting if the system determines that the user likely has a moderately severe, severe, or profound degree of hearing impairment, despite the user perceiving only a mild-to-moderate level of hearing handicap.

Some examples of queries can include those of the Hearing Handicap Inventory for the Elderly (HHIE), the Hearing Handicap Inventory for Adults (HHIA), Hearing Assistive Technology (HAT) Needs Questionnaire, or another type of questionnaire related to one or more of hearing capabilities, perceived hearing handicap, case history, lifestyle, and specific listening needs. Aspects of exemplary hearing assessment procedures are described in greater detail below.

In some embodiments, an individual can be discouraged or prevented from proceeding with an automated or partially automated hearing device fitting if the system determines that the user likely does not have a mild to moderate hearing impairment according to the Hearing Handicap Inventory for the Elderly (HHIE). Table 2 below shows an exemplary interpretation chart for the HHIE test.

TABLE 2

| Score | Score Interpretation |
| --- | --- |
| 0-8 | No Hearing Handicap |
| 10-24 | Mild-Moderate Handicap |
| 26-40 | Severe Handicap |

In some cases, the device wearer evaluation 610 can include evaluating settings for previous hearing assistance devices used by the device wearer. For example, evaluating settings for previous hearing assistance devices can include determining maximum gain values from previous hearing assistance devices. If the maximum gain values cross a threshold value, then the system can determine that the device wearer may not be a good candidate for a self-fitting procedure. Similarly, if the settings for previous hearing assistance devices reveal a complexity that is a hallmark of a complex hearing pathology or handicap, then the then the system can determine that the device wearer may not be a good candidate for a self-fitting procedure.

While not shown in this flow chart, device wearer evaluation can also occur at other points in the overall process. For example, device wearer evaluation can occur in between operations of the self-fitting procedure. In some embodiments, device wearer evaluation can also occur at the end of the self-fitting procedure. In some embodiments, device wearer evaluation can be determined based upon one or more of the hearing device wearer's preference(s) and test performance(s) during the fitting procedure. For example, the hearing device wearer, in at least one embodiment, may be permitted to evaluate settings that could suggest that the hearing device wearer is not a good candidate to perform a fitting in the absence of a hearing professional.

In another operation, if the device wearer does not meet a threshold value based on the device wearer evaluation, then the device wearer can be disqualified 612. In some cases, the device wearer can be provided with information on how they can proceed, such as contacting a hearing professional, returning their device, etc. In some embodiments, the user may be provided with contact information for specific hearing professionals within a geographic area deemed convenient for the hearing assistance device wearer, using any suitable methods known in the art.

In another operation, if the device wearer meets a threshold value based on the device wearer evaluation, then the device wearer can proceed with the fitting procedure 614, which can include various operations as described elsewhere herein.

In some embodiments, aspects of the fitting process can be reinitiated at later time points after an initial fitting. In some embodiments, a method can include reinitiating the operations of receiving input from the hearing assistance device wearer and determining a maximum power output of the hearing assistance device that does not exceed a loudness discomfort level (LDL) at a later time point. In some embodiments, the later time point is at least 30 minutes, 1 hour, 2 hours, 4 hours, 8 hours, 24 hours, 48 hours, 72 hours, 1 week, 4 week, 3 months, 6 months, or a 1 year or longer after the initial operations of receiving input from the hearing assistance device wearer and determining a maximum power output of the hearing assistance device. In some embodiments a method can include reinitiating the operations of presenting the device wearer with a series of audio samples and questions regarding content of the same and receiving answers to the questions from the device wearer at a later time point. In some embodiments, a method can include reinitiating the operations of recording speech from the device wearer and evaluating the recorded speech to classify the degree or configuration of hearing loss of the device wearer at a later time point.

Figure 7:
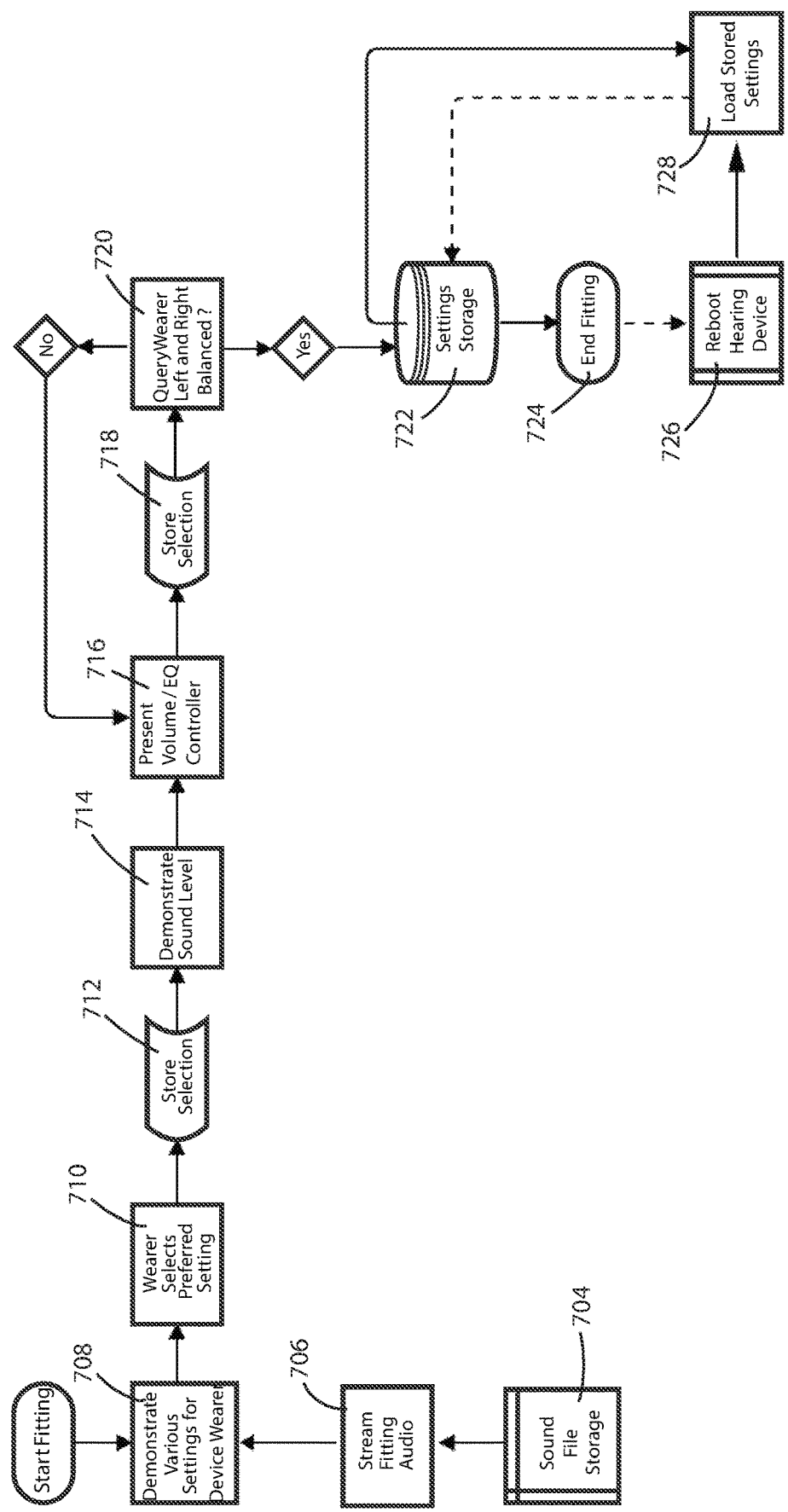
FIG. 7 is a flow chart of a method of fitting a hearing assistance device in accordance with various embodiments herein.

It will be appreciated that fitting procedures can include various specific steps or operations. Referring now to FIG. 7, a flow chart is shown of a method of fitting a hearing assistance device in accordance with various embodiments herein. The method can include demonstrating 708 various settings for the device wearer. Settings can include, but are not limited to, amplification (gain) values at one or more frequencies (which can include bass/treble balance), compression thresholds, speeds and knee points or ratios at one or more frequencies, delay settings at one or more frequencies, frequency shifting strategies, noise reduction methods, speech enhancement methods, speech or tonal indictor volumes, and the like. In some embodiments, settings can specifically be related to frequencies corresponding to specific speech sounds (such as Ling speech sounds). One example of frequencies is provided in Table 3 below.

TABLE 3

| Ling Speech Sound | Exemplary Frequency |
|---|---|
| "mmm" | 250-500 Hz |
| "ooo" | 350 (F1) and 900 (F2) Hz |
| "ahh" | 700 (F1) and 1300 (F2) Hz |
| "eee" | 300 (F1) and 2500 (F2) Hz |
| "shh" | 2-4 kHz |
| "sss" | 3.5-7 kHz |

While the audio sample needed to demonstrate the settings or instructions to the device wearer can be provided in various ways, in some embodiments, the audio sample can be streamed 706. The audio sample to be streamed can be retrieved from sound file storage 704 which can be part of a separate device or network node. It will be appreciated that any suitable device can be operatively connected and stream the audio sample and/or instructions. Streaming the audio sample or instructions to the hearing assistance device can include streaming wirelessly, through wired connectivity, or through a combination of wired and wireless connectivity. In some cases, audio samples and/or instructions to the user can be provided by accessing data stored in memory on the hearing assistance device or another device connected thereto or otherwise generated internally by the hearing assistance device. In some cases, audio samples and/or instructions to the user can be played through a speaker of an external device in addition to or instead of being played through a speaker of the hearing assistance device. In some cases, audio samples and/or instructions to the user can be provided by a device that is acoustically coupled to the hearing assistance device. In some cases, audio samples can be provided by prompting one or more of the device wearer and an individual other than the device wearer to generate the audio sample.

In some embodiments, the system can receive and evaluate settings for previous hearing assistance devices used by the device wearer and then use these previous settings as a starting point for settings in the new device. For example, gain values at particular frequencies, frequency shifting values, and maximum power output of the hearing assistance device that does not exceed a loudness discomfort level (LDL) from previous hearing assistance devices can all be used to set appropriate starting points during the fitting procedure.

Next, the device wearer can select 710 preferred settings. After that, the preferred settings can be stored 712. Then sounds levels can be demonstrated 714 for the device wearer. Then, controls such as a volume control and/or equalizer control 716 can be presented to the user and the system can receive their selections and then store 718 the selections. The device wearer can then be queried regarding appropriate left/right balance 720. If not appropriate, then the hearing device wearer can be returned to the volume control and/or equalizer control 716 to adjust left/right balance. However, the left/right balance is appropriate, then the settings can be saved in memory and/or a database for settings storage 722. After that, the fitting process can end 724. In some cases, the hearing device can be rebooted 726, after which the device can load 728 stored settings. However, in some cases, depending on architecture, the hearing device can load or otherwise implement new settings without rebooting.

Figure 8:
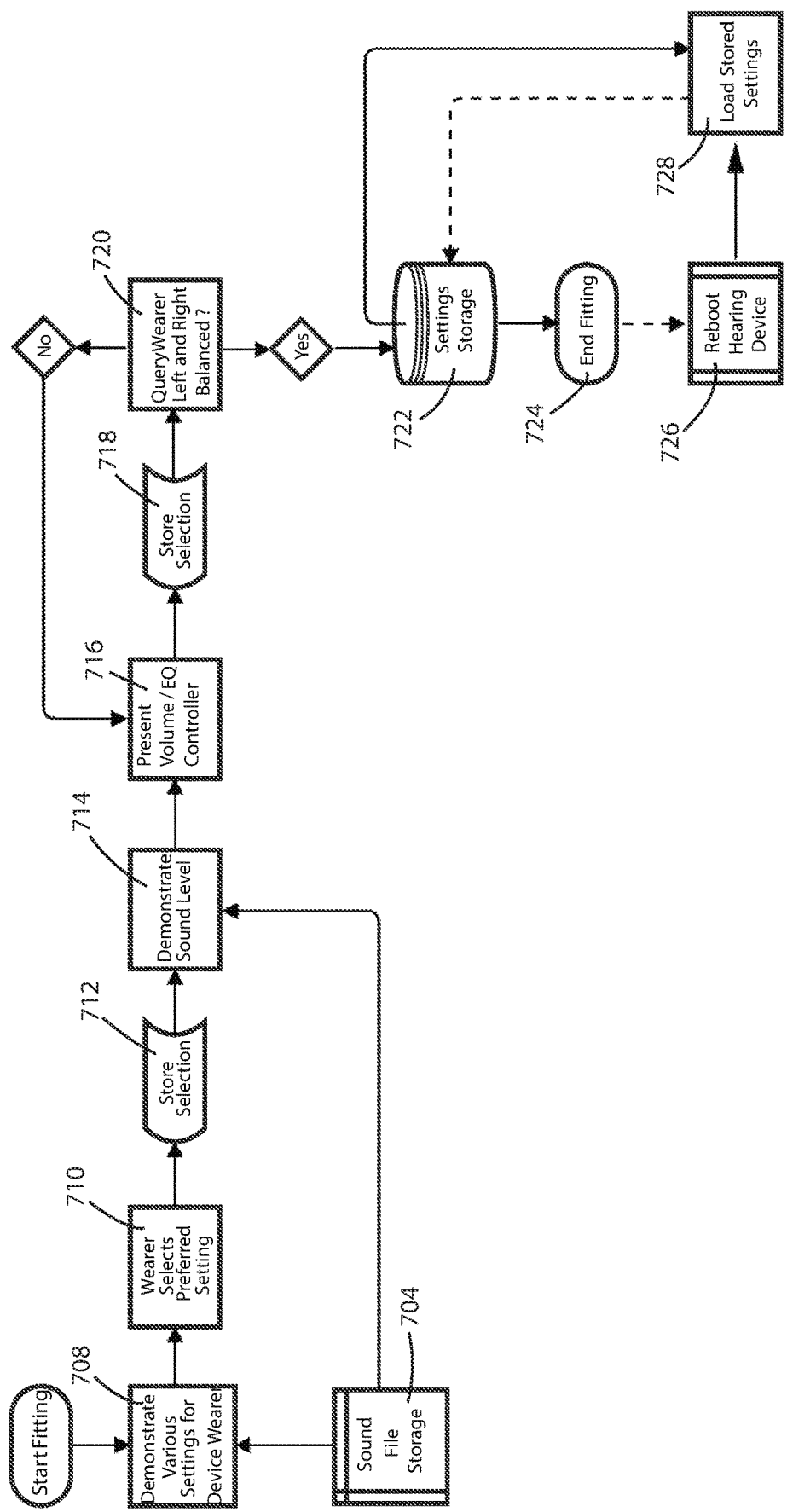
FIG. 8 is a flow chart of a method of fitting a hearing assistance device in accordance with various embodiments herein.

In the embodiment shown in FIG. 7, the audio sample or instructions to the user to create sound or speak needed to demonstrate the settings was retrieved from sound file storage 704 and streamed 706 (wirelessly, through wired connectivity, or through a combination of wired and wireless connectivity). However, it will be appreciated, that in some embodiments, the audio sample or instructions may not be streamed. For example, the audio sample or instructions may be stored in memory directly on the hearing assistance device. Referring now to FIG. 8, a flow chart is shown of a method of fitting a hearing assistance device in accordance with various embodiments herein. The elements shown in FIG. 8 are generally similar to FIG. 7, however, in this embodiment the streaming aspect is omitted. Rather, the audio sample and/or instructions are pulled from sound file storage 704 and played without being streamed.

Figure 9:
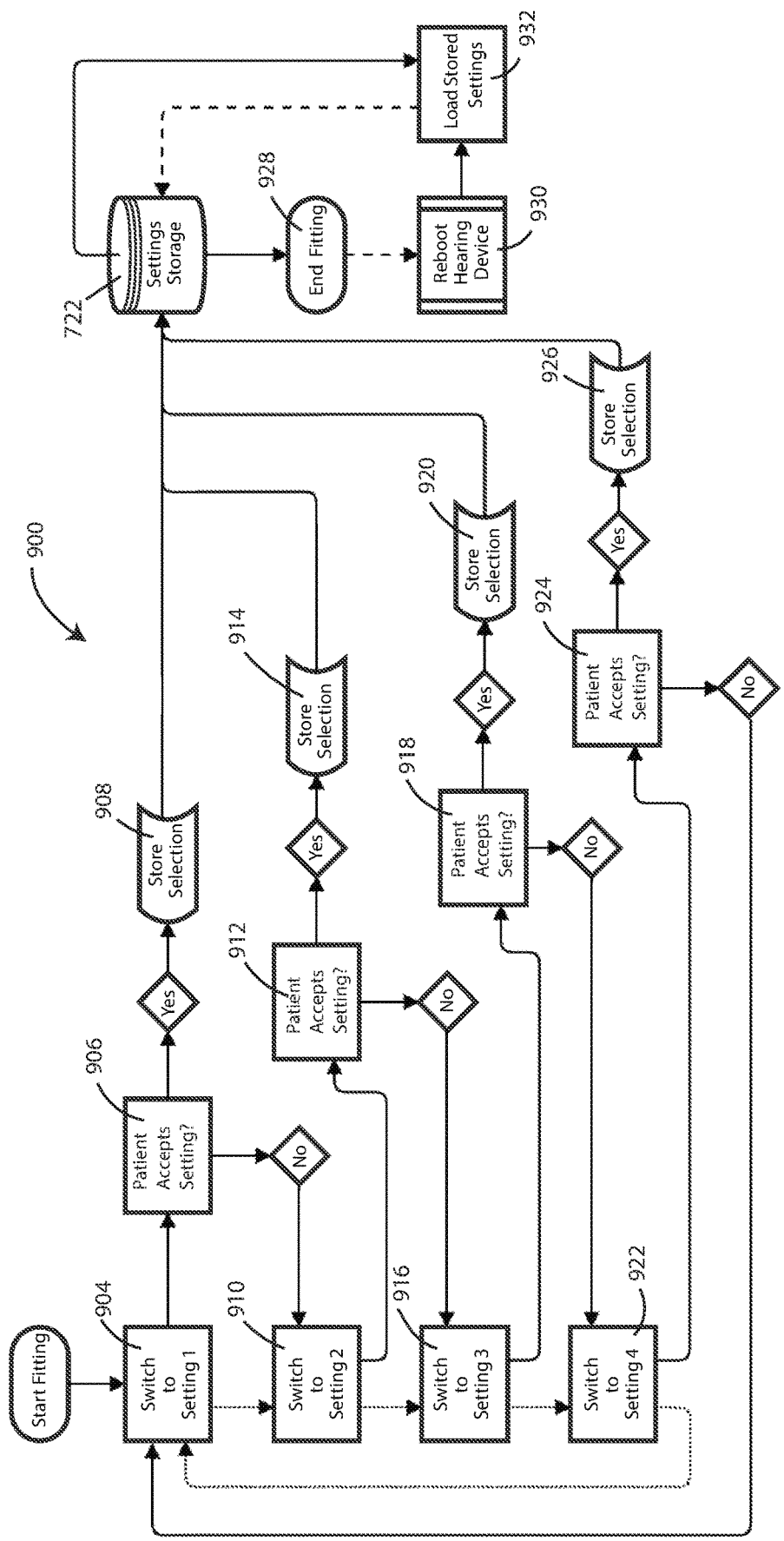
FIG. 9 is a flow chart of a method of fitting a hearing assistance device in accordance with various embodiments herein.

As described previously, values for multiple parameters/settings may be selected during the fitting process. In some embodiments, the selected values can be stored after each value is selected. In some cases, the device wearer is presented with a series of parameters values until one is accepted. Referring now to FIG. 9, a flow chart is shown of a method 900 of fitting a hearing assistance device in accordance with various embodiments herein. The device may offer a first setting value ("setting 1") 904. Then, the device wearer (or patient) has an opportunity to accept the setting value 906. If accepted, then the settings are stored 908 in settings storage 722. If the settings are not accepted then the device may offer a second setting value ("setting 2") 910. Then, the device wearer (or patient) has an opportunity to accept the setting value 912. If accepted, then the settings are stored 914 in settings storage 722. If the settings are not accepted then the device may offer a third setting value ("setting 3") 916. Then, the device wearer (or patient) has an opportunity to accept the setting value 918. If accepted, then the settings are stored 920 in settings storage 722. If the settings are not accepted then the device may offer a third setting value ("setting 4") 922. Then, the device wearer (or patient) has an opportunity to accept the setting value 924. If accepted, then the settings are stored 926 in settings storage 722. If not accepted, then the process can return to presenting the first setting value ("setting 1") again.

Then, the fitting process can be ended 928 and after that the hearing device can be rebooted 930. Then stored settings can be loaded 932 and device operation can proceed.

Figure 10:
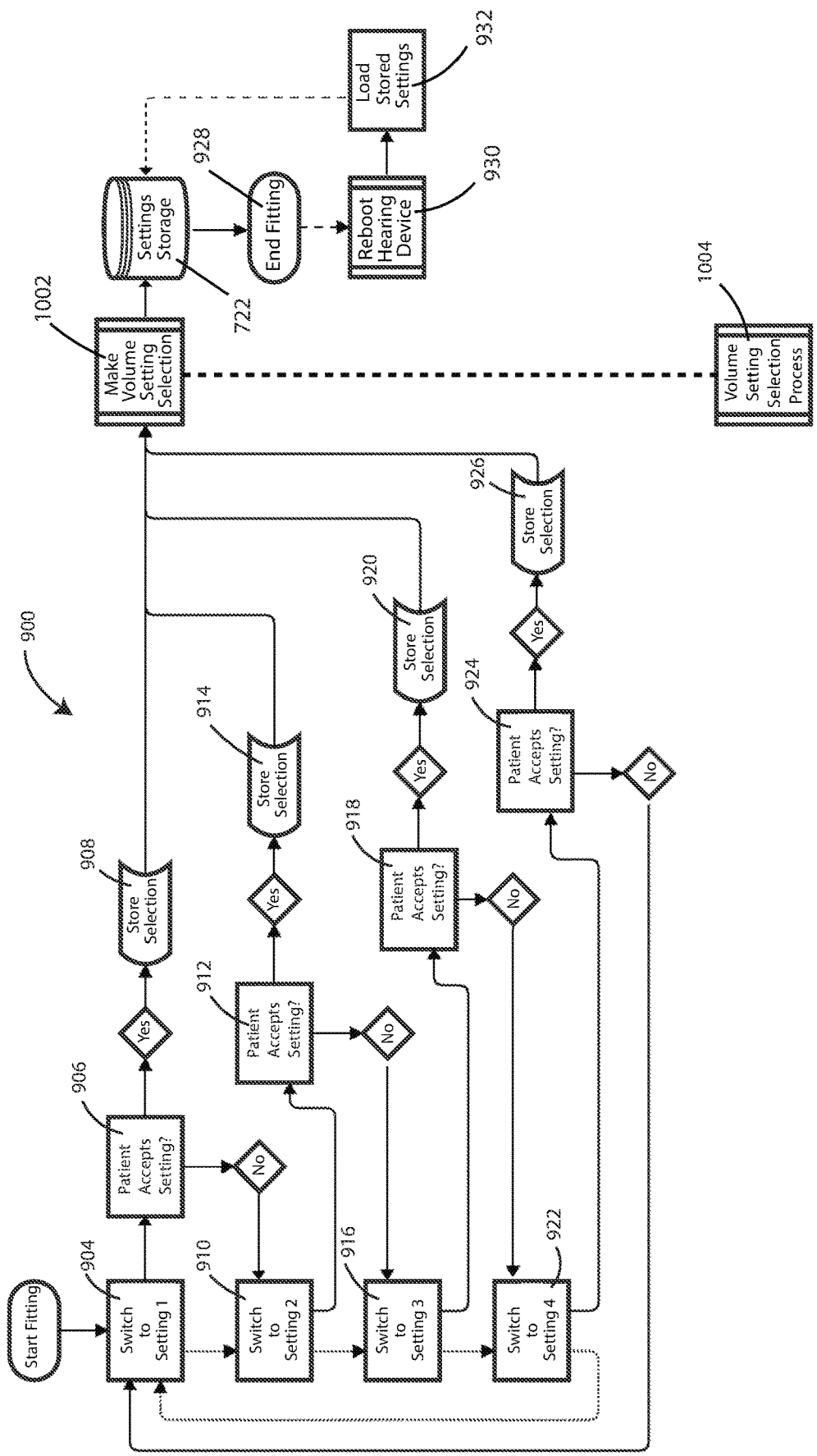
FIG. 10 is a flow chart of a method of fitting a hearing assistance device in accordance with various embodiments herein.

Referring now to FIG. 10, a flow chart is shown of a method of fitting a hearing assistance device in accordance with various embodiments herein. The method illustrated in FIG. 10 is generally similar to that of FIG. 9. However, in this embodiment, a volume setting selection 1002 is made before settings are stored. The volume setting selection can proceed in various ways. One example of a volume setting selection process 1004 is described in FIG. 11.

Figure 11:
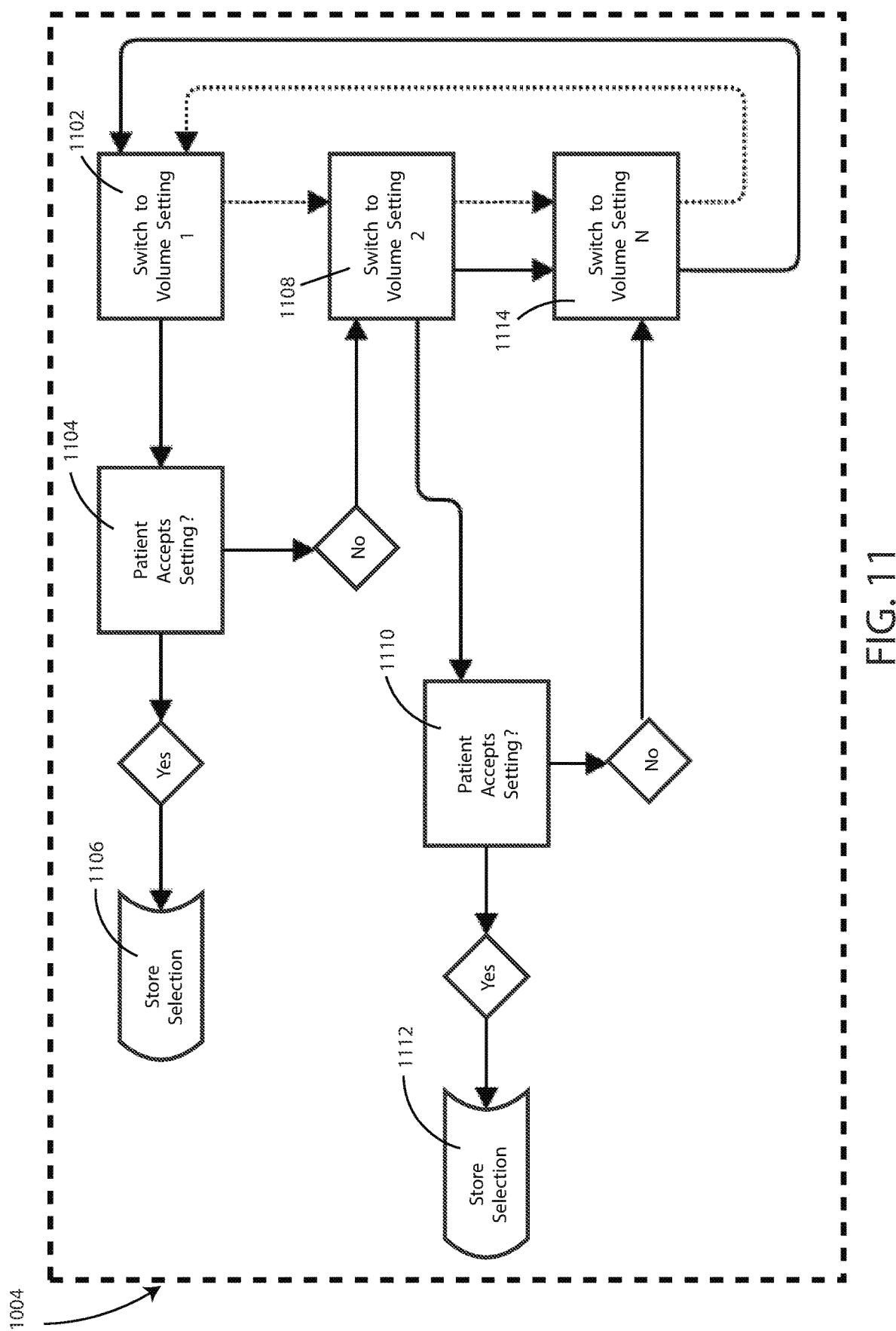
FIG. 11 is a flow chart of a method of a volume setting selection process in accordance with various embodiments herein.

Referring now to FIG. 11, a flow chart is shown of a method of a volume setting selection process 1004 in accordance with various embodiments herein. The selection process 1004 can include presenting a first volume setting ("setting 1") 1102. Then, the device wearer (or patient) has an opportunity to accept the setting value 1104. If accepted, then the settings are stored 1106 in settings storage. If the settings are not accepted then the device may offer a second setting value ("setting 2") 1108. Then, the device wearer (or patient) has an opportunity to accept the setting value 1110. If accepted, then the settings are stored 1112 in settings storage. If the settings are not accepted then the device may offer another setting value ("setting N") 1114, followed similarly by an opportunity to accept the value and store it or presentation of yet another setting value. This process can proceed until a setting value is accepted. In various embodiments, this procedure can be used to determine a maximum power output of the hearing assistance device that does not exceed a loudness discomfort level (LDL).

Figure 12:
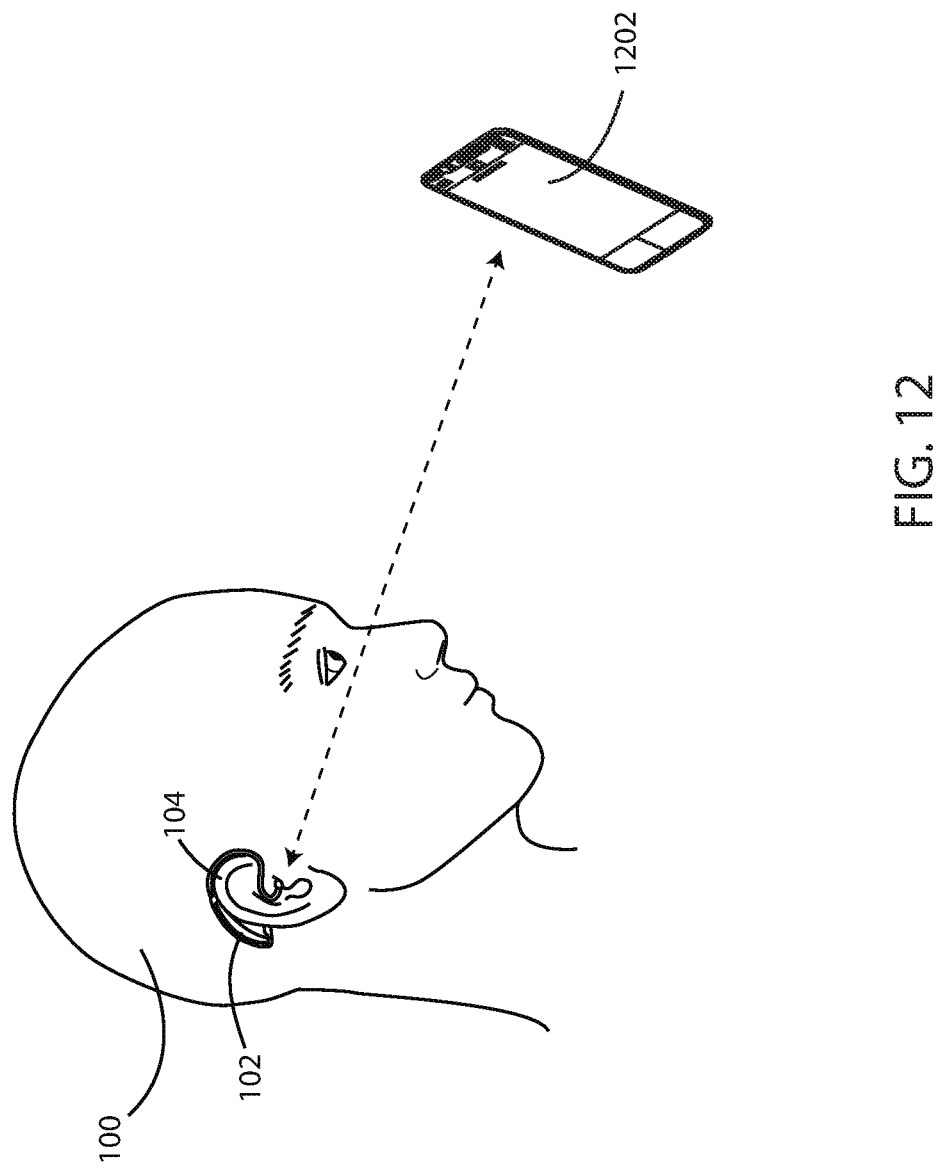
FIG. 12 is a schematic view of a device user with an external device in accordance with various embodiments herein.

As described previously, some embodiments herein can utilize a separate device for the fitting process such as a smartphone or a hearing device accessory. The separate device can be used for various purposes including, but not limited to, a source of streaming audio data, a visual/audible/tactile source for prompting, queries, information display, a device for receiving selections/responses from the device wearer, etc. Referring now to FIG. 12, a schematic view is shown of a device wearer 100, wearing a hearing assistance device 102 on or about their ear 104, with an external display device 1202 in accordance with various embodiments herein. In some cases, the external device can include a microphone, a speaker, and a display screen.

In various embodiments, the device wearer 100 can interface with the external device 1202 (such as illustrated with respect to FIGS. 13-16 herein). In some embodiments, the external device 1202 can receive input from the hearing assistance device wearer (such in response to queries discussed herein can through interface objects such as button) and can then send programming data to the hearing assistance device based on the received input. In some cases, the programming data directly reflects inputs provided by the device wearer. In some cases, the external device takes the inputs from the device wearer and then translates or converts the inputs into device setting values. For example, the external device can convert the received input from the hearing assistance device wearer and the determined maximum power output into the device setting values.

The device setting values can be specific to the type of hearing assistance device and/or to the hardware configuration of the hearing assistance device. By way of example, a given device hardware configuration includes a specific hearing assistance device type (see examples above including RIC, BTE, etc.), along with a specific model, along with a various hardware pieces such as a receiver, domes (ear buds), ear molds, tubing, and the like. For example, RIC (receiver-in-canal) hearing assistance devices may include receivers with varying gain values (40 gain, 50 gain, 60 gain, 70 gain, etc.). In some cases, different receivers can have different frequency response curves. Such receivers can be swappable and include an electrical identification that the hearing assistance device can read when connected. Lower gain options are smaller, which allows them to fit in more ears, but may not provide enough amplification for every user without creating distortion. Higher gain options are larger, but can provide more amplification for patients with greater degrees of hearing loss. Domes may come in open-fit, occluded, and power styles. Ear molds can allow for specific amounts of acoustic venting ranging from open-fit to occluded.

Each of these components can impact the nature of sound provided to the device wearer and can be considered when translating or converting the inputs from the device wearer into device setting values. For example, if a device wearer has a hardware configuration including a high gain value receiver, then user inputs may be scaled appropriately to achieve desirable levels of sound output from the receiver.

In some cases, a look-up table can be stored which can then be accessed when converting or translating from received inputs to device setting values. In some cases, the look-up table can be stored as part of a fitting application operating on an external device. In some cases, the look-up table can be stored within the memory of the hearing assistance device itself. In some cases, the look-up table can be remotely stored and then queried when needed through commands across a data network, such as the Internet.

In some embodiments, data regarding the configuration of the hearing device components can be programmed into the memory of the hearing device by its manufacturer, distributor, or retailer. In some embodiments, a database containing device-specific component configuration data may referenced. In some embodiments, the database containing device-specific component configuration data may be populated by one or more of a hearing device ordering system software, a hearing device production management software, and the like. In some embodiments, device-specific component configuration data may be manually indicated by the user. In some embodiments, device-specific component configuration data can be automatically detected by one or more the hearing device, hearing device accessory, hearing device programmer, hearing device programming software, and the like. In an illustrative example, a hearing device can automatically detect the type of receiver (and cable) attached to the hearing device by reading a resistive identification tag from the attached receiver (and cable). In other embodiments, one or more radio frequency identification tags can be read from hearing device components and used to automatically detect the likely configuration of the hearing device or to filter the available configuration options to simplify a manual selection process performed by an individual.

In some embodiments, programming data can be sent from the external device across a data network to a server in a remote location, the programming data can be based on the received input from the hearing assistance device wearer and the determined maximum power output. In some embodiments, a method can further include sending device settings from the remote location back to the hearing assistance device, wherein the device settings are determined based on the received input from the hearing assistance device wearer and/or the determined maximum power output.

Figure 13:
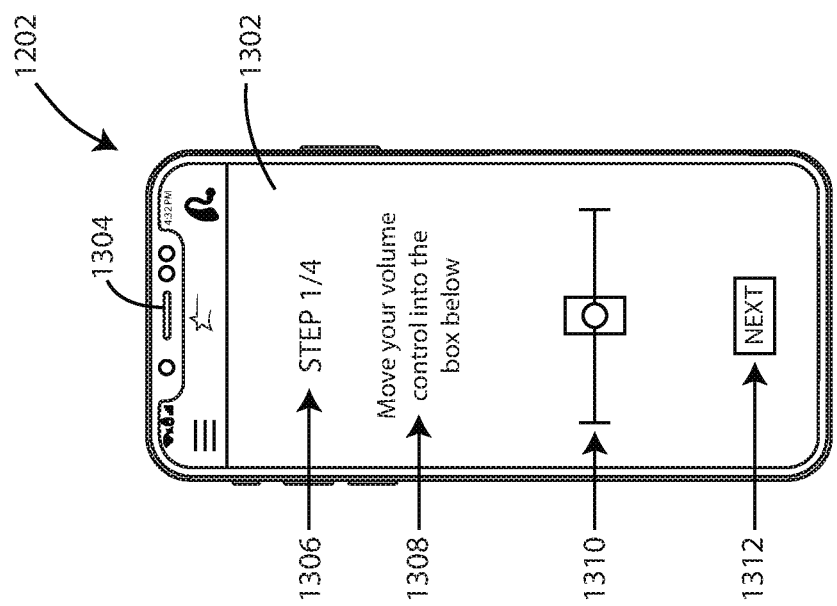
FIG. 13 is a schematic view of an external device in accordance with various embodiments herein.

Referring now to FIG. 13, a schematic view is shown of an external device 1202 in accordance with various embodiments herein. The external device 1202 includes a display screen 1302, which can be a video display screen and in some embodiments a touch screen for accepting input from the device wearer. The external device 1202 can further include a speaker 1304 and microphone (not shown in this view).

Various pieces of information can be displayed on the display screen. In some embodiments, a progress indicator 1306 can be displayed including an indication of what step or operation the fitting process is currently on and/or an indication of the total number of steps or operations in the fitting process. In some embodiments, an instruction 1308 can also be provided to the device wearer. In some embodiments, a video can be shown providing the device wearer with clear instructions for placing the hearing assistance device(s) in their ear. It will be appreciated that the instruction can also be provided audibly, via the external device 1202 and/or the hearing assistance device(s). In various embodiment, a control interface 1310 can also be provided.

In the example shown in FIG. 13, the control interface 1310 can be a volume control slider, to allow the user to change the volume on their external device 1202 so that audio sample(s) can be provided at a sufficient volume. However, in some embodiments, this initial operation of adjusting the external device 1202 volume can be omitted. In various embodiments, a step/operation advancement button 1312 can also be included.

Figure 14:
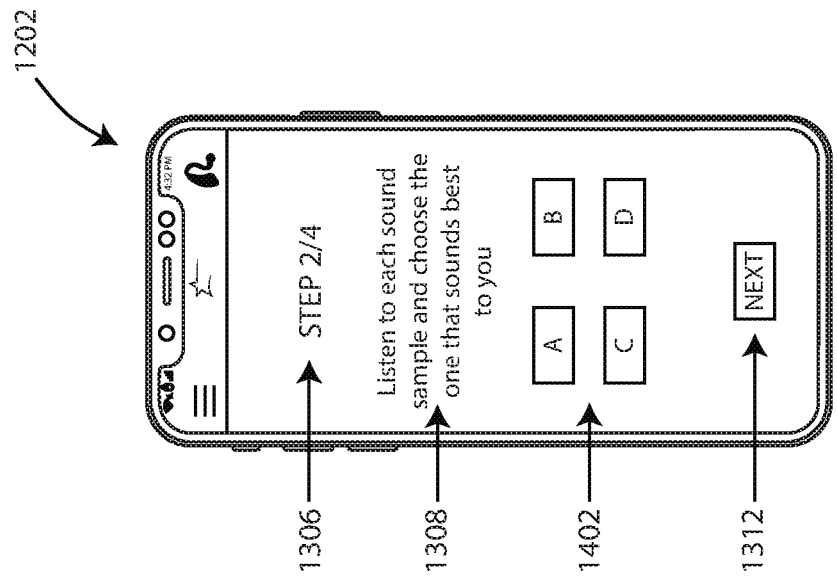
FIG. 14 is a schematic view of an external device in accordance with various embodiments herein.

Referring now to FIG. 14, a schematic view is shown of an external device in accordance with various embodiments herein. In this view, the instruction 1308 can instruct the device wearer to listen to audio samples and select the one that sounds best. In this view, a control interface 1402 can include a plurality of buttons representing different parameters. These buttons can represent options for values for various parameters. Pushing these buttons can result in presentation of audio files that are configured to provide the same input but are processed to be amplified based on a specific hearing loss configuration. In some cases, the audio file can loop continuously for the user to evaluate. In some cases, the sound file can include a male voice, a female voice, and/or samples of words at different frequency levels low, mid and/or high.

In some embodiments, the audio files can be configured to represent different examples of bass/treble balance and this operation can include presenting the hearing assistance device wearer with a plurality of preselected bass/treble balance settings and receiving input from the hearing assistance device wearer regarding preference. However, in some embodiments, instead of preselected bass/treble balance settings, the user can be presented with an interface that allows a continuous range of adjustments for bass/treble balance, such as a slider control, a wheel control, or the like.

In some cases, preselected options can be selected for presentation to the device wearer based on an evaluation of factors and pattern matching. By way of example, a database can be maintained including bass/treble balance settings and factors such as location, country, gender, age, family history, genealogical factors, genotype, and the like. Then, a pattern matching algorithm can be applied in order to determine the most likely bass/treble balance settings based on the factors (location, country, gender, age, family history, genealogical factors, genotype, and the like) specific to the device wearer. This approach can also be applied for other types of options that may be presented to a device wearer in accordance with embodiments herein.

Referring now to FIG. 15, a schematic view is shown of an external device in accordance with various embodiments herein. In this view, the instruction 1308 can instruct the device wearer to listen to audio samples and select the one that sounds best. In this view, a control interface 1502 can include a plurality of buttons representing different parameters. These buttons can represent options for values for various parameters. In some cases, the operation illustrated in FIG. 15 builds on the operation illustrated in FIG. 14, by offering a subset of listening options based on the previous choice to better narrow in on an optimal device configuration.

Referring now to FIG. 16, a schematic view is shown of an external device in accordance with various embodiments herein. In this view, the instruction 1308 can instruct the device wearer to toggle between the right and left and adjust the volume so that the audio is perceived to have a same loudness in each ear (binaural balance). An audio file can be played during this operation. In this view, a control interface 1602 can include a control to start the audio as well as a control to set the balance between the right and the left ears. After the operations are completed, the selected hearing aid parameters can be sent to and stored by the hearing assistance device and implemented for use going forward. Then, in some embodiments, the hearing assistance device can be rebooted.

In some embodiments, aspects illustrated in FIG. 16, can include receiving input from the hearing assistance device wearer with an external device regarding a binaural balance including presenting the hearing assistance device wearer with a first plurality of preselected binaural balance settings and receiving input from the hearing assistance device wearer regarding which one they prefer. In some embodiments, methods can further include presenting the hearing assistance device wearer with a second plurality of preselected binaural balance settings based on received input from the hearing assistance device wearer regarding which one they prefer. However, in some embodiments, instead of preselected options, the user can be presented with an interface that allows a continuous range of adjustments for binaural balance, such as a slider control, a wheel control, or the like.

Figure 17:
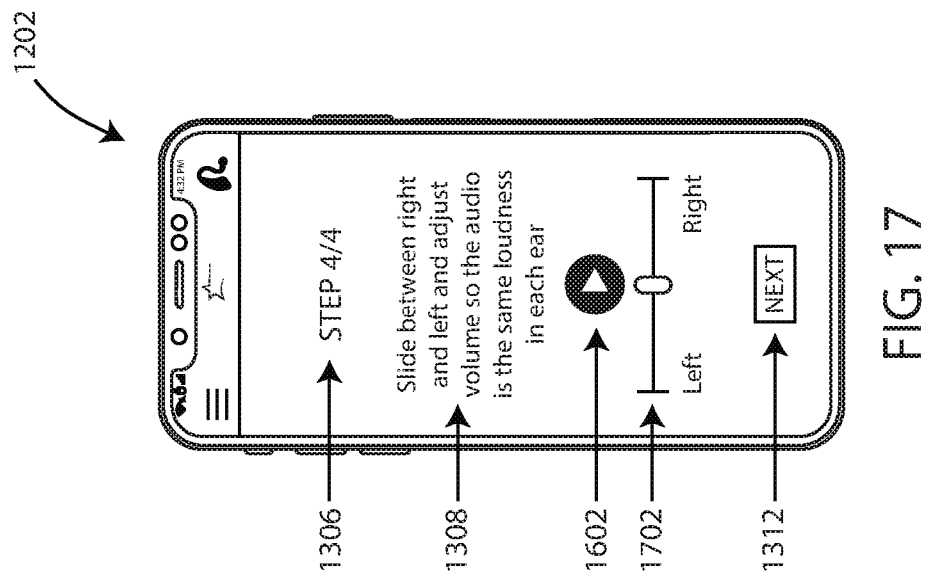
FIG. 17 is a schematic view of an external device in accordance with various embodiments herein.

Referring now to FIG. 17, a schematic view is shown of an external device in accordance with various embodiments herein. FIG. 17 is generally similar to FIG. 16. However, in FIG. 17 a slider control 1702 is included. The device wearer can be presented with one or more audio samples with the relative loudness on each side (e.g., right vs. left) controlled by the position of the slider control 1702. The device wearer can be asked to adjust the slider until the perceived loudness on each side is the same and the resulting slider position can be used to set a value for binaural balance. If the device wearer cannot determine a position at which perceived loudness is the same and/or if the device wearer perceives loudness to be the same at all or most positions then, in some embodiments, the properties of the sound samples can be changed (change in frequency spectrum, change in the nature of the sound samples, etc.) and the step can be repeated. In some embodiments, if the device wearer cannot determine a position at which perceived loudness is the same and/or if the device wearer perceives loudness to be the same at all or most positions then operations can be performed to evaluate the environment and/or the device wearer further, such as described herein with respect to FIG. 6 and the operations referred to therein including, but not limited to, 604 and/or 610.

As described above, some potential device wearers may have a hearing loss that is so substantial, debilitating, or otherwise complicated in nature that they are not a good candidate for working with a device to perform a fitting in the absence of a hearing professional. Some potential device wearers may have physical, emotional, neurological, or cognitive limitations which could prevent them from being a good candidate to perform a fitting in the absence of a hearing professional. In some municipalities, there may be specific laws, regulations, or guidance that may specify the candidacy criteria for fittings performed in the absence of a hearing professional. Qualifying the hearing status/candidacy of the device wearer may help to ensure that it is appropriate for the device wearer to proceed with an automated or partially automated fitting procedure. As such, some embodiments herein can also include systems and devices that can evaluate or qualify the hearing status and candidacy of the device wearer (e.g., detect the degree and/or nature of hearing loss and perceived hearing impairment) to ensure that it is sufficient to proceed with a proper fitting procedure in the absence of a hearing professional.

In some embodiments, the system may use global positioning or other location determination techniques to determine where the fitting is occurring. In some embodiments, the system may access a database to determine location-specific or municipality-specific laws, regulations, or guidance that may specify the candidacy criteria for a fitting performed in the absence of a hearing professional. In some embodiments, the system can adapt or terminate a fitting procedure in accordance with the location-specific or municipality-specific laws, regulations, or guidance accessed through the database. In some embodiments, the system may use global positioning or other location determination techniques to determine where the hearing devices are being used. In some embodiments, the system can adapt hearing device parameters or disable a hearing device in accordance with the location-specific or municipality-specific laws, regulations, or guidance assessed through the database. In some embodiments, operations relating to the use of global positioning or other location determination techniques may conform to preferences of the device manufacturer, distributor, retailer, and the like.

As referenced in FIG. 6 above, if the device wearer does not meet a threshold value based on the device wearer evaluation, then the device wearer can be disqualified from proceeding with the fitting process. However, in some embodiments, rather than terminating the process entirely, the system can invoke the remote assistance of a hearing device professional to assist in proceeding through the fitting process.

Figure 18:
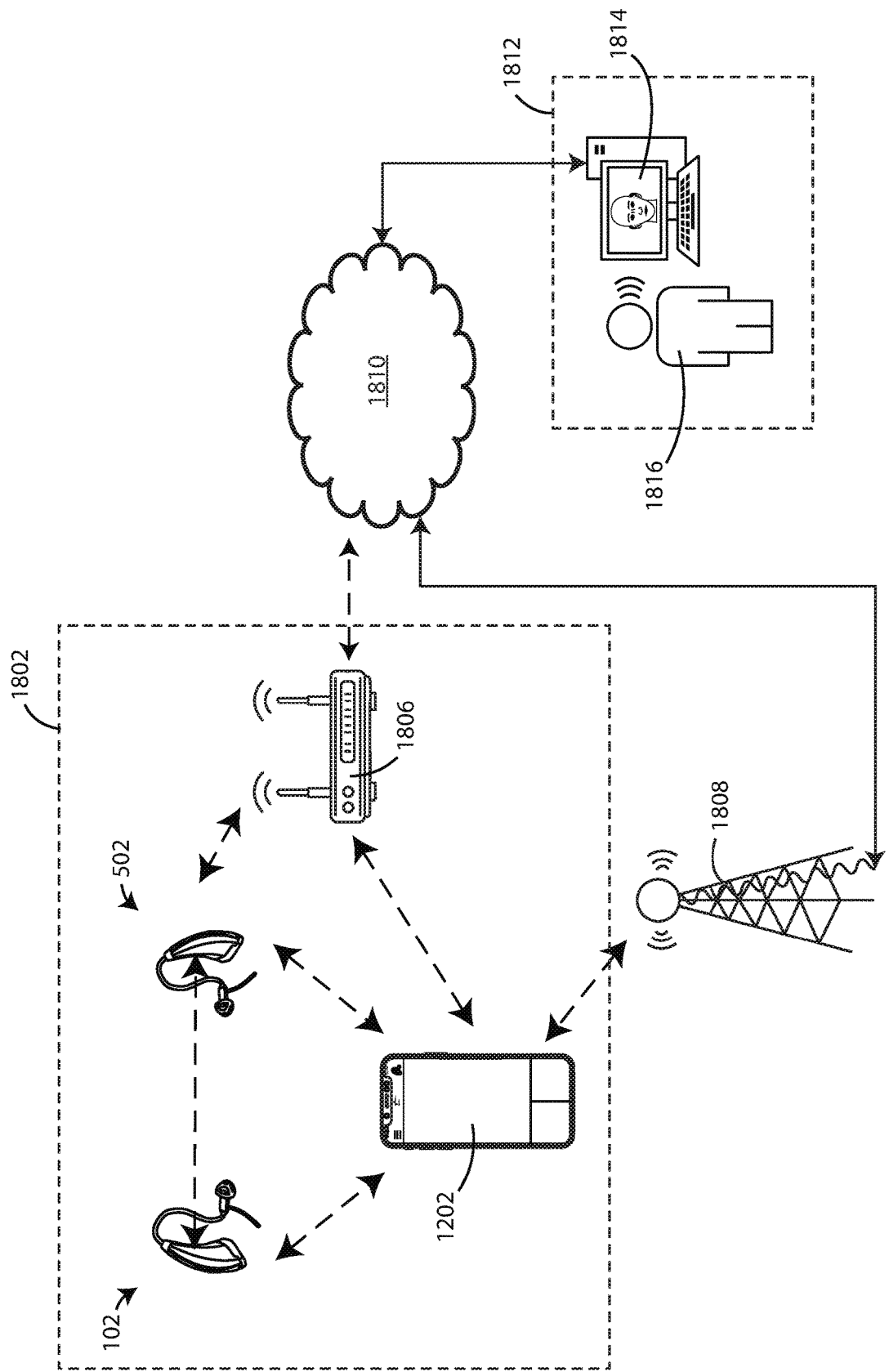
FIG. 18 is a schematic view of a system including communications to and from a hearing professional to assist with a fitting process in accordance with various embodiments herein.

Referring now to FIG. 18, a schematic view is shown of a system including communications to and from a hearing professional to assist with a fitting process in accordance with various embodiments herein. In a first location 1802, a device wearer can have a first hearing assistance device 102 and, in some cases, a second hearing assistance device 502. In various embodiments, data and/or signals can be exchanged directly between the first hearing assistance device 102 and the second hearing assistance device 502. An external display device 1202 with a video display screen, such as a smartphone, can also be disposed within the first location 1802. The external display device 1202 can exchange data and/or signals with one or both of the first hearing assistance device 102 and the second hearing assistance device 502 and/or with an accessory to the hearing assistance devices (e.g., a remote microphone, a remote control, a phone streamer, etc.). The external display device 1202 can also exchange data across a data network to the cloud 1810, such as through a wireless signal connecting with a local gateway device, such as a network router 1806 or through a wireless signal connecting with a cell tower 1808 or similar communications tower. In some embodiments, the external display device 1202 can also connect to a data network to provide communication to the cloud 1810 through a direct wired connection.

In some embodiments, a hearing professional 1816 (such as an audiologist) can receive information from devices at the first location 1802 remotely at a second location 1812 through a data communication network such as that represented by the cloud 1810. The hearing professional 1816 can use a computing device 1814 to see and interact with the information received. The received information can include, but is not limited to, information regarding hearing assessment scores, the patient's history, the specific model of the hearing assistance device, and the like. In some embodiments, received information can be provided to the hearing professional 1816 in real time. In some embodiments, received information can be stored and provided to the hearing professional 1816 at a later time point.

In some embodiments, the hearing professional 1816 can send information remotely from the second location 1812 through a data communication network such as that represented by the cloud 1810 to devices at the first location 1802. For example, the hearing professional 1816 can enter information into the computing device 1814, can use a camera connected to the computing device 1814 and/or can speak into the external computing device. The sent information can include, but is not limited to, instructions on what operation to take next with the fitting procedure, programming data including values for device settings to try, and the like. In some embodiments, feedback information from the hearing professional 1816 can be provided to the subject in real time. In some embodiments, received information can be stored and provided to the subject at a later time point.

Hearing assistance devices herein, external devices herein, and the systems that hearing assistance devices and/or external devices are part of can be configured to execute various operations. In particular, hearing assistance devices herein, external devices herein, and the systems that hearing assistance devices and/or external devices are part of can be configured to execute all or any of the various operations that may elsewhere herein be described as method steps or operations.

Hearing assistance devices herein can include, but are not limited to, behind-the-ear (BTE), in-the ear (ITE), in-the-canal (ITC), invisible-in-canal (IIC), receiver-in-canal (RIC), receiver in-the-ear (RITE) and completely-in-the-canal (CIC) type hearing assistance devices. In some embodiments, the hearing assistance device can be a hearing aid falling under 21 C.F.R. § 801.420 or similar regulations. In another example, the hearing assistance device can include one or more Personal Sound Amplification Products (PSAPs). In another example, the hearing assistance device can include one or more cochlear implants, cochlear implant magnets, cochlear implant transducers, and cochlear implant processors. In another example, the hearing assistance device can include one or more "hearable" devices that provide various types of functionality. In other examples, hearing assistance device can include other types of devices that are wearable in, on, or in the vicinity of the user's ears. In other examples, hearing assistance devices can include other types of devices that are implanted or otherwise osseointegrated with the user's skull; wherein the hearing assistance device is able to facilitate stimulation of the wearer's ears via the bone conduction pathway.

Figure 19:
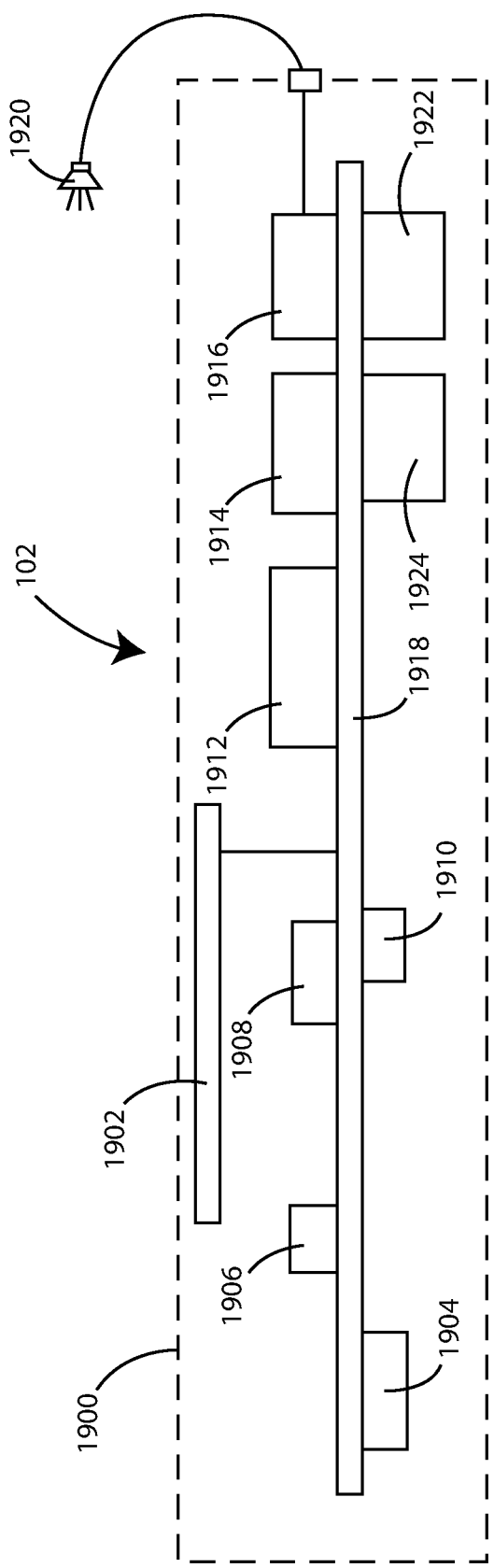
FIG. 19 is a schematic view of components of a hearing assistance device in accordance with various embodiments herein.

Hearing assistance devices herein can include various components. Referring now to FIG. 19, a schematic view is shown of components of a hearing assistance device in accordance with various embodiments herein. The block diagram of FIG. 19 represents a generic ear-worn device for purposes of illustration. The hearing assistance device 102 can include several components electrically connected to a mother circuit 1918 (e.g., flexible or non-flexible mother board) which is disposed within housing 1900. A power supply circuit 1904 can include a battery and can be electrically connected to the mother circuit 1918 and provides power to the various components of the hearing assistance device 102. One or more microphones 1906 are electrically connected to the mother circuit 1918, which provides electrical communication between the microphones 1906 and a digital signal processor (DSP) 1912. Among other components, the DSP 1912 incorporates or is coupled to audio signal processing circuitry configured to implement various functions described herein. A sensor package 1914 can be coupled to the DSP 1912 via the mother circuit 1918. The sensor package 1914 can include one or more different specific types of sensors such as those described in greater detail below. In some embodiments, one or more user switches 1910 (e.g., on/off, volume, mic directional settings) are electrically coupled to the DSP 1912 via the mother circuit 1918.

An audio output device 1916 is electrically connected to the DSP 1912 via the mother circuit 1918. In some embodiments, the audio output device 1916 comprises a speaker (coupled to an amplifier). In other embodiments, the audio output device 1916 comprises an amplifier coupled to an external receiver 1920 adapted for positioning within an ear of a wearer. The external receiver 1920 can include an electroacoustic transducer, speaker, or loud speaker. The hearing assistance device 102 may incorporate a communication device 1908 coupled to the mother circuit 1918 and to an antenna 1902 directly or indirectly via the mother circuit 1918. The communication device 1908 can be a BLUETOOTH® transceiver, such as a BLE (BLUETOOTH® low energy) transceiver or other transceiver (e.g., an IEEE 802.11 compliant device, 900 MHz, NFMI, etc.). The communication device 1908 can be configured to communicate with one or more external devices, such as those discussed previously, in accordance with various embodiments. In various embodiments, the communication device 1908 can be configured to communicate with an external visual display device such as a smartphone, a video display screen, a tablet, a computer, a virtual reality display device, an augmented reality display device, or the like.

In various embodiments, the hearing assistance device 102 can also include a control circuit 1922 and a memory storage device 1924. The control circuit 1922 can be in electrical communication with other components of the device. The control circuit 1922 can execute various operations, such as those described herein. The control circuit 1922 can include various components including, but not limited to, a microprocessor, a microcontroller, an FPGA (field-programmable gate array) processing device, an ASIC (application specific integrated circuit), or the like. The memory storage device 1924 can include both volatile and non-volatile memory. The memory storage device 1924 can include ROM, RAM, flash memory, EEPROM, SSD devices, NAND chips, and the like. The memory storage device 1924 can be used to store data from sensors as described herein and/or processed data generated using data from sensors as described herein, including, but not limited to, information regarding hearing status, wearer candidacy, instructions for fitting procedures, performance of the same, data regarding setting properties, and the like. In some embodiments, the control circuit 1922 can include a geolocation circuit such as a GPS circuit, a cell site triangulation circuit, a circuit that uses IP address to determine location, or the like.

Methods

Many different methods are contemplated herein. Aspects of system/device operation described elsewhere herein can be performed as operations of one or more methods in accordance with various embodiments herein. In addition, methods and method steps/operation described below and elsewhere herein can be executed by systems and devices herein as operations wherein the system/device is configured to execute those steps/operations.

In a first aspect, a method of fitting a hearing assistance device is included, the method including providing an audio sample to a hearing assistance device wearer, receiving input from the hearing assistance device wearer regarding a preferred sound volume (or perceived loudness), receiving input from the hearing assistance device wearer with the external device regarding a bass/treble balance, and determining a maximum power output of the hearing assistance device that does not exceed a loudness discomfort level (LDL).

In a second aspect, in addition to one or more of the preceding or following aspects, or in the alternative to some aspects, a method can include receiving input from the hearing assistance device wearer regarding a binaural balance.

In a third aspect, in addition to one or more of the preceding or following aspects, or in the alternative to some aspects, a method can further include receiving input from the hearing assistance device wearer using an external device and sending programming data from the external device to the hearing assistance device based on the received input.

In a fourth aspect, in addition to one or more of the preceding or following aspects, or in the alternative to some aspects, the programming data can include device setting values, wherein an external device converts received input from the hearing assistance device wearer and the determined maximum power output into the device setting values, and the device setting values are specific to the type of hearing assistance device.

In a fifth aspect, in addition to one or more of the preceding or following aspects, or in the alternative to some aspects, a method can further include sending data from the external device across a data network to a server in a remote location, the data based on the received input from the hearing assistance device wearer and the determined maximum power output.

In a sixth aspect, in addition to one or more of the preceding or following aspects, or in the alternative to some aspects, a method can further include sending device settings from the remote location back to the hearing assistance device, wherein the device settings are determined based on the received input from the hearing assistance device wearer and the determined maximum power output.

In a seventh aspect, in addition to one or more of the preceding or following aspects, or in the alternative to some aspects, an external device used with systems and methods herein includes a speaker.

In an eighth aspect, in addition to one or more of the preceding or following aspects, or in the alternative to some aspects, an external device used with systems and methods herein includes a microphone, a speaker and a display screen.

In a ninth aspect, in addition to one or more of the preceding or following aspects, or in the alternative to some aspects, an external device can be a smartphone or a tablet device.

In a tenth aspect, in addition to one or more of the preceding or following aspects, or in the alternative to some aspects, receiving input from the hearing assistance device wearer with the external device regarding a bass/treble balance includes presenting the hearing assistance device wearer with a first plurality of preselected bass/treble balance settings and receiving input from the hearing assistance device wearer regarding preference.

In an eleventh aspect, in addition to one or more of the preceding or following aspects, or in the alternative to some aspects, a method can further include presenting the hearing assistance device wearer with a second plurality of preselected bass/treble balance settings based on received preference input.

In a twelfth aspect, in addition to one or more of the preceding or following aspects, or in the alternative to some aspects, receiving input from the hearing assistance device wearer regarding a binaural balance can include presenting the hearing assistance device wearer with a first plurality of preselected binaural balance settings and receiving input from the hearing assistance device wearer regarding which one they prefer.

In a thirteenth aspect, in addition to one or more of the preceding or following aspects, or in the alternative to some aspects, a method can further include presenting the hearing assistance device wearer with a second plurality of preselected binaural balance settings based on received input from the hearing assistance device wearer regarding which one they prefer.

In a fourteenth aspect, in addition to one or more of the preceding or following aspects, or in the alternative to some aspects, a hearing assistance device can be a hearing aid under 21 C.F.R. § 801.420 or similar regulations.

In a fifteenth aspect, in addition to one or more of the preceding or following aspects, or in the alternative to some aspects, an operation of receiving input from the hearing assistance device wearer with the external device regarding a bass/treble balance occurs after an operation of receiving input from the hearing assistance device wearer with the external device regarding a preferred sound volume (or perceived loudness).

In a sixteenth aspect, in addition to one or more of the preceding or following aspects, or in the alternative to some aspects, an operation of receiving input from the hearing assistance device wearer with the external device regarding a bass/treble balance occurs before the operation of receiving input from the hearing assistance device wearer with the external device regarding a preferred sound volume (or perceived loudness).

In a seventeenth aspect, in addition to one or more of the preceding or following aspects, or in the alternative to some aspects, an operation of receiving input from the hearing assistance device wearer with the external device regarding a binaural balance occurs after the operation of determining a maximum power output of the hearing assistance device that does not exceed a loudness discomfort level.

In an eighteenth aspect, in addition to one or more of the preceding or following aspects, or in the alternative to some aspects, an operation of receiving input from the hearing assistance device wearer with an external device regarding a binaural balance occurs before the operation of determining a maximum power output of the hearing assistance device that does not exceed a loudness discomfort level.

In a nineteenth aspect, in addition to one or more of the preceding or following aspects, or in the alternative to some aspects, an operation of providing an audio sample to a hearing assistance device wearer includes at least one of: wirelessly streaming the audio sample to the hearing assistance device, accessing data stored on the hearing assistance device representing the audio sample, playing the audio sample through a speaker of an external device, and prompting an individual to generate the audio sample.

In a twentieth aspect, in addition to one or more of the preceding or following aspects, or in the alternative to some aspects, wirelessly streaming the audio sample to the hearing assistance device further includes playing the audio sample through a speaker forming part of the hearing assistance device.

In a twenty-first aspect, in addition to one or more of the preceding or following aspects, or in the alternative to some aspects, prompting an individual to generate the audio sample further includes monitoring the sounds generated by the individual for sound volume.

In a twenty-second aspect, in addition to one or more of the preceding or following aspects, or in the alternative to some aspects, prompting an individual to generate the audio sample includes providing specific instructions for generating sound.

In a twenty-third aspect, in addition to one or more of the preceding or following aspects, or in the alternative to some aspects, prompting an individual to generate the audio sample includes providing a script for the individual to follow or mimic.

In a twenty-fourth aspect, in addition to one or more of the preceding or following aspects, or in the alternative to some aspects, prompting an individual to generate the audio sample includes prompting the device wearer to generate sounds to ensure that the wearer is comfortable with his or her own voice.

In a twenty-fifth aspect, in addition to one or more of the preceding or following aspects, or in the alternative to some aspects, the operation of providing an audio sample to a hearing assistance device wearer includes both streaming the audio sample to the hearing assistance device and playing the audio sample through the speakers of an external device.

In a twenty-sixth aspect, in addition to one or more of the preceding or following aspects, or in the alternative to some aspects, a method can further include qualifying the device wearer based on the severity of their hearing impairment or based on a perceived hearing handicap.

In a twenty-seventh aspect, in addition to one or more of the preceding or following aspects, or in the alternative to some aspects, qualifying the device wearer can include verifying that the device wearer has a hearing loss that is less than profound.

In a twenty-eighth aspect, in addition to one or more of the preceding or following aspects, or in the alternative to some aspects, qualifying the device wearer can include verifying that the device wearer has a hearing loss that is less than severe.

In a twenty-ninth aspect, in addition to one or more of the preceding or following aspects, or in the alternative to some aspects, qualifying the device wearer can include presenting the device wearer with a panel of queries directed to the severity of their hearing impairment or their perceived hearing handicap and receiving feedback from the device wearer regarding the same.

In a thirtieth aspect, in addition to one or more of the preceding or following aspects, or in the alternative to some aspects, a method can further include estimating the severity of their hearing impairment or their perceived hearing handicap based on the device wearer's feedback.

In a thirty-first aspect, in addition to one or more of the preceding or following aspects, or in the alternative to some aspects, presenting the device wearer with a panel of queries directed to the severity of their hearing impairment or their perceived hearing handicap can be performed prior to providing an audio sample to a hearing assistance device wearer.

In a thirty-second aspect, in addition to one or more of the preceding or following aspects, or in the alternative to some aspects, qualifying the device wearer can include presenting the device wearer with a series of audio samples and questions regarding content of the same.

In a thirty-third aspect, in addition to one or more of the preceding or following aspects, or in the alternative to some aspects, a series of audio samples can include at least one of a phoneme confusion test, a California Consonant Test, a Chear Auditory Perception test, and a speech-in-noise test.

In a thirty-fourth aspect, in addition to one or more of the preceding or following aspects, or in the alternative to some aspects, a series of audio samples and questions regarding content of the same can be administered as part of a game.

In a thirty-fifth aspect, in addition to one or more of the preceding or following aspects, or in the alternative to some aspects, a method can further include qualifying the device wearer based on settings for a previous device configured for the device wearer.

In a thirty-sixth aspect, in addition to one or more of the preceding or following aspects, or in the alternative to some aspects, a method can further include qualifying a sound field in which the device wearer is present.

In a thirty-seventh aspect, in addition to one or more of the preceding or following aspects, or in the alternative to some aspects, qualifying the sound field includes evaluating at least one of evaluating echoes, reverberation time, decay time, critical distance, room impulse measure, absorption coefficient across a human detectable frequency band, ambient noise, comb filter distortion, coloration distortion, early reflection, and late reflection.

In a thirty-eighth aspect, in addition to one or more of the preceding or following aspects, or in the alternative to some aspects, qualifying the sound field includes emitting a sample sound and evaluating sound received at the hearing assistance device.

In a thirty-ninth aspect, in addition to one or more of the preceding or following aspects, or in the alternative to some aspects, a sample sound can be emitted from an external device.

In a fortieth aspect, in addition to one or more of the preceding or following aspects, or in the alternative to some aspects, evaluating sound received at the hearing assistance device includes comparing the sample sound with the sound received across a human detectable frequency band.

In a forty-first aspect, in addition to one or more of the preceding or following aspects, or in the alternative to some aspects, the audio sample provided to the hearing assistance device wearer can be manipulated based on acoustic properties of the sound field in which the hearing assistance device wearer is located.

In a forty-second aspect, in addition to one or more of the preceding or following aspects, or in the alternative to some aspects, manipulations of an audio sample can include changing a delay in the audio sample.

In a forty-third aspect, in addition to one or more of the preceding or following aspects, or in the alternative to some aspects, a method can further include presenting the device wearer with a series of audio samples and questions regarding content of the same; and receiving answers to the questions from the device wearer.

In a forty-fourth aspect, in addition to one or more of the preceding or following aspects, or in the alternative to some aspects, a method can further include calculating an accuracy score based the received answers and initiating a corrective measure if the accuracy score crosses a threshold value.

In a forty-fifth aspect, in addition to one or more of the preceding or following aspects, or in the alternative to some aspects, a corrective measure can include notifying the device wearer that they should contact a care provider and terminating the fitting procedure.

In a forty-sixth aspect, in addition to one or more of the preceding or following aspects, or in the alternative to some aspects, a method can further include recording speech from the device wearer and evaluating the recorded speech to classify the degree or configuration of hearing loss of the device wearer.

In a forty-seventh aspect, in addition to one or more of the preceding or following aspects, or in the alternative to some aspects, a method can further include requesting the device wearer to speak a plurality of words prior to the operation of recording speech from the device wearer.

In a forty-eighth aspect, in addition to one or more of the preceding or following aspects, or in the alternative to some aspects, a method can further include determining a location of the device wearer, evaluating regulations for device fitting based on the location, and terminating or modifying the fitting procedure or notifying the device wearer that they should contact a care provider based on the regulation.

In a forty-ninth aspect, in addition to one or more of the preceding or following aspects, or in the alternative to some aspects, a method can further include reinitiating the operations of receiving input from the hearing assistance device wearer and determining a maximum power output of the hearing assistance device that does not exceed a loudness discomfort level (LDL) at a later time point.

In a fiftieth aspect, in addition to one or more of the preceding or following aspects, or in the alternative to some aspects, a later time point is at least 1, 2, 4, 8, 12, 16, 24, 48, 72 or 96 hours after the initial operations of receiving input from the hearing assistance device wearer and determining a maximum power output of the hearing assistance device.

In a fifty-first aspect, in addition to one or more of the preceding or following aspects, or in the alternative to some aspects, a method can further include reinitiating the operations of presenting the device wearer with a series of audio samples and questions regarding content of the same and receiving answers to the questions from the device wearer at a later time point. The later time point can be minutes, hours or days later. Such as 1, 2, 4, 8, 12, 16, 24, 48, 72, 96, or more hours later.

In a fifty-second aspect, in addition to one or more of the preceding or following aspects, or in the alternative to some aspects, a method can further include reinitiating the operations of recording speech from the device wearer and evaluating the recorded speech to classify the degree or configuration of hearing loss of the device wearer at a later time point. The later time point can be minutes, hours or days later. Such as 1, 2, 4, 8, 12, 16, 24, 48, 72, 96 or more hours later.

In a fifty-third aspect, in addition to one or more of the preceding or following aspects, or in the alternative to some aspects, a method can further include activating a frequency lowering/shifting algorithm on the hearing assistance device if a test result based on "s" and "sh" phonemes crosses a threshold value. It will be appreciated that in some languages (such as tonal languages) these particular examples may not be speech sounds, but a similar principal could still be applied and/or in various embodiments other phonemes can be tested for confusion.

In a fifty-fourth aspect, in addition to one or more of the preceding or following aspects, or in the alternative to some aspects, a method can further include activating a frequency lowering/shifting algorithm on the hearing assistance device if a test result based on "s" and "sh" phonemes crosses a threshold value and high-frequency gain values on the hearing assistance device are maxed out or otherwise should not be increased. It will be appreciated that in some languages (such as tonal languages) these particular examples may not be speech sounds, but a similar principal could still be applied and/or in various embodiments other phonemes can be tested for confusion.

Hearing Assessment Procedures

In various embodiments herein, hearing assessment procedures can be used to determine the hearing capabilities of a device wearer. Such assessment procedures can be performed at various points in time. In some embodiments, such assessment procedures can be performed prior to a fitting procedure. In some embodiments, such assessments can be performed during a fitting procedure. In some embodiments, such assessments can be performed after a fitting procedure In some cases, assessment procedures can include administering one or more specific tests such as a phoneme confusion test, a California Consonant Test, and a Chear Auditory Perception test, a speech-in-noise test, a Hearing Assistive Technology (HAT) Needs Checklist, or the like. Administration of the tests (one or more) can result in a score that can be used to qualify the device wearer as being an appropriate candidate for the device wearer. Whether or not the device wearer is considered to pass can be based on whether or not the resulting score crosses a threshold value. In some cases, the tests can result in a score reflecting the percentage of correct answers.

In various embodiments, the threshold value for allowing the device wearer to continue with the fitting procedure can be about 5, 10, 20, 30, 40, 50, 55, 60, 65, 70, 75, 80, 85, 90, 95, or 98 percent, or an amount falling within a range between any of the foregoing.

In some embodiments, tests can be administered to the device wearer before and after the fitting procedure and the resulting change can be evaluated. In some cases, if the final score after the fitting procedure is not sufficiently high, the device wearer may be informed that they are not a good candidate and the fitting process may terminate.

In some cases, the device wearer may receive a recommendation to purchase or use one or more of a hearing device accessory or assistive listening technology, such as a remote microphone device, media streamer, etc. In some cases, the hearing device may be automatically programmed to include at least one setting that enables the wearer to use e.g., a telecoil or magnetic sensor within an induction hearing loop or any other type of compatible assistive listening system audio stream, such as BLUETOOTH®.

In some cases, the device wearer may receive a referral to a hearing professional. In some cases, a hearing professional at a remote location may be contacted in real time to assist with the fitting process.

In some embodiments, the threshold value representing the difference between an initial score and a score after the fitting procedure can be about 10, 15, 20, 25, 30, 35, 40, 45, 50, 55, 60, 65, or 70 percentage points, or an amount falling within a range between any of the foregoing.

One test that can be used includes the California Consonant Test (CCT). The CCT is a closed set consonant phoneme recognition test. The words are provided as audio (through the hearing assistance device, through an external device with a speaker, or by another person) and then the device wearer must select the correct word (audibly, through a touch interface associated with an external device, or in another way). Exemplary alternatives for a plurality of groups are shown below in Table 4.

TABLE 4

|  | Word 1 | Word 2 | Word 3 | Word 4 |
| --- | --- | --- | --- | --- |
| Group 1 | Cow | Owl | House | Mouse |
| Group 2 | Bed | Hen | Peg | Egg |
| Group 3 | Fan | Man | Cat | Hat |
| Group 4 | Key | Three | Feet | Sheep |
| Group 5 | Pig | Chick | Fish | Ship |
| Group 6 | Horse | Ball | Fork | Door |
| Group 7 | Shoe | Moon | Spoon | Food |
| Group 8 | Pipe | Pie | Kite | Five |
| Group 9 | Sock | Cot | Doll | Dog |
| Group 10 | Jug | Duck | Bus | Cup |

Another test that can be applied includes the Chear Auditory Perception Text (CAPT). The CAPT is a four-alternative-forced-choice monosyllabic word-discrimination test. The words are spoken and then the testing subject must select the correct word. Exemplary alternatives for a plurality of groups are shown below in Table 5.

TABLE 5

|  | Word 1 | Word 2 | Word 3 | Word 4 |
| --- | --- | --- | --- | --- |
| Group 1 | Mat | Bat | Cat | Fat |
| Group 2 | Wine | Wise | White | Wipe |
| Group 3 | Fin | Tin | Shin | Chin |
| Group 4 | Stork | Talk | Chalk | Fork |
| Group 5 | Bun | Bug | Bud | Buzz |
| Group 6 | Kick | Tick | Thick | Pick |
| Group 7 | White | Right | Light | Night |
| Group 8 | Law | Raw | War | Your |
| Group 9 | What | Wash | Want | Watch |
| Group 10 | Jug | Drug | Bug | Mug |
| Group 11 | Cheap | Cheat | Cheek | Cheese |
| Group 12 | Caught | Call | Corn | Core |

Another test that can be applied includes the Ling Test. The Ling Test provides a quick and accurate assessment of a subject's ability to hear across the frequencies (broadly—250 to 8000 Hz) essential for spoken language. The test includes isolated phonemes to target low, middle, and high frequency sounds. The phonemes for the Ling Six Sound Test are [m], [ah], [oo], [ee], [sh] and [s]. Similar to as with other tests, words can be spoken and then the testing subject can pick what they believe to be the correct answer. As referenced above, the Ling Test can also include periods of silence. In the language of some hearing device users, a different speech sound test may, similarly, be used to determine the audibility of certain speech sounds of various intensities and/or frequency composition within the typical ranges of human hearing.

In some cases, errors with phonemes such as [sh] and [s], in particular, can inform settings/enablement of frequency lowering and/or frequency shifting strategies. By way of example, in some cases a frequency lowering algorithm can be applied in order to assist devices wearers that have demonstrated problems with the phonemes [sh] and [s]. Such an algorithm can include monitoring high-frequency regions for spectral peaks that are responsible for the recognition of phonemes such as [sh] and [s], then characterizing the high-frequency spectral shape and dynamically recreating that spectral shape inside a lower frequency target region, in which the hearing device user may have a greater degree of hearing sensitivity and/or less distortion.

The source frequency range for analysis and target frequency range for the shift can be set as parameters within the system. In some embodiments, the source frequency range for analysis can be from about 2, 2.5, 3, 3.5, 4, 4.5, 5, 5.5, or 6 kHz to about 3, 3.5, 4, 4.5, 5, 5.5, 6, 6.5, 7, 7.5, 8, 10, 12, 14, 16, 18, 20, or 22 kHz, or a range between any of the foregoing. In some cases, the target frequency range is about 0.5, 1, 1.5, 2, 2.5, 3, 3.5, 4, 4.5, or 5 kHz lower than the source frequency range. In some cases, the system can determine whether a device wearer is likely to benefit from such a frequency lowering algorithm according to criteria including one or more of: hearing thresholds below 1000 Hz are 55 db HL or better; high-frequency hearing loss slope is greater than or equal to 25 dB HL per octave; a single hearing threshold between 1000 Hz and 3000 Hz must be 55 dB HL or worse; all hearing thresholds between 4000 Hz and 8000 Hz must be 55 dB HL or worse. Aspects of such frequency lowering/shifting algorithms are described in U.S. Pat. Nos. 8,526,650; 8,761,422, and U.S. Publ. Appl. No. 2018/0103328, the content of which is herein incorporated by reference. In some embodiments, lowering frequency ranges may be performed for reasons going beyond improving speech understanding. For example, some frequencies may be lowered for better spatial awareness.

In some embodiments, a frequency lowering/shifting algorithm on the hearing assistance device can be activated if test results based on certain phonemes such as [s] and [sh] cross a threshold value. In some embodiments, a frequency lowering/shifting algorithm on the hearing assistance device can be activated if test results based on certain phonemes such as [s] and [sh] cross a threshold value and high-frequency gain values on the hearing assistance device are maxed out or otherwise should not be increased. In some embodiments, a frequency lowering/shifting algorithm on the hearing assistance device can be activated if test results based on certain phonemes such as [s] and [sh] cross a threshold value and at least one of the following criteria is met: high-frequency gain is maxed out due to receiver or system limits, a high level of gain causes distortion of the receiver, a high level of gain causes distortion of the user's auditory system, high-frequency gain is maxed out due to uncomfortable loudness level (UCL) perceptions of the user; and high-frequency gain cannot be increased without producing feedback oscillations.

In various embodiments, devices herein can also perform feedback testing including playing sounds through a speaker or electroacoustic transducer and measuring the amount of such sound detected through microphones of the hearing assistance device (e.g., measuring the feedback). Such testing can be performed at various steps of procedures described herein. In various embodiments, if the feedback exceeds a threshold value, this can serve as a limit on gain.

Another test that can be applied includes the Nonsense Syllable Test (NST). The NST (also known as the Edgerton-Danhauer Nonsense Syllable Test) is considered similar to a word recognition or speech discrimination test. It was developed because of negative clinical and research experiences with traditional word test materials. It is a close-set speech recognition test involving the identification of consonants that are presented in a framework of meaningless consonant-vowel (CV) and vowel-consonant (VC) syllables. It is designed to concentrate on the kinds of consonant confusion errors that are the most likely to occur.

Further tests that can be applied include speech-in-noise tests. Speech-in-noise tests can include the QuickSIN (Quick Speech-in-noise Test) or HINT (Hearing in Noise Test), or the like. The QuickSIN typically consists of a series of IEEE (Institute of Electrical and Electronics Engineers) sentences presented in a background of four-talker babble. The level of the sentences typically remains fixed while the noise level varies. Sentences are typically presented at a loud most comfortable level (MCL) (either 75 or 80 dB HL) while the signal-to-noise ratio (SNR) is typically varied in 5-dB steps starting at +25 SNR. Typically, five key words are scored in each sentence and one point is given for each key word repeated correctly. The number of key words correct is typically subtracted from the reference 25.5 dB. This score is commonly referred to as the SNR loss. The HINT consists of modified BKB (Bamford-Kowal-Bench) sentences that are typically delivered in groups of 10. Speech-shaped noise is typically used as the competing background noise. Typically, the patient must repeat all the key words of a sentence for a response to be considered correct. The HINT typically requires that the background noise remain fixed, usually at 65 dB sound pressure level (SPL), while the presentation level of the sentences typically varies in 2-dB steps. It will be appreciated that many different types of tests of hearing are contemplated herein.

It will also be appreciated that in-situ testing, by the hearing device system, may not require strict adherence to one or more of the customary conventions of the various, controlled laboratory or clinical tests, alluded to in the various sections of this disclosure, in order to achieve the desired results. As an illustration, according to at least one embodiment, the voices of individuals, speaking in proximity to the hearing device user, may be treated as the competing noise for an exemplary in-situ speech-in-noise test. It will be appreciated that, in this case, the number of individuals speaking, the intensity and spectral composition of each voice, the phonemic balance, the angle(s) of onset, envelope modulations of the speech, room acoustics characteristics, and the like may be more dynamic or different in real-world listening situations than what is commonly represented in the various formalized test protocols relied upon as conceptual references.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method of fitting a hearing assistance device comprising:
    providing an audio sample to a hearing assistance device wearer;
    determining a degree of hearing impairment of the hearing assistance device wearer;
    comparing the determined degree of hearing impairment to a threshold level of impairment;
    preventing the hearing assistance device wearer from continuing a device fitting process if the determined degree of hearing impairment is greater than the threshold level of impairment;
    qualifying a sound field in which the hearing assistance device wearer is present;
    manipulating the audio sample provided to the hearing assistance device wearer based on acoustic properties of the sound field;
    receiving input from the hearing assistance device wearer regarding a preferred sound volume or perceived loudness;
    receiving input from the hearing assistance device wearer regarding a bass/treble balance; and
    determining a maximum power output of the hearing assistance device that does not exceed a loudness discomfort level (LDL).

2. The method of claim 1, further comprising receiving input from the hearing assistance device wearer regarding a binaural balance using an external device and sending programming data from the external device to the hearing assistance device based on the received input, the programming data comprising device setting values, wherein the external device converts the received input from the hearing assistance device wearer and the determined maximum power output into the device setting values, wherein the device setting values are specific to a type of hearing assistance device.

3. The method of claim 1, wherein receiving input from the hearing assistance device wearer regarding a bass/treble balance comprises presenting the hearing assistance device wearer with a first plurality of preselected bass/treble balance settings and receiving input from the hearing assistance device wearer regarding preference.

4. The method of claim 3, further comprising presenting the hearing assistance device wearer with a second plurality of preselected bass/treble balance settings based on received preference input.

5. The method of claim 1, wherein the operation of providing an audio sample to a hearing assistance device wearer comprises at least one of
    wirelessly streaming the audio sample to the hearing assistance device;
    playing the audio sample through an induction loop and receiving an audio sample signal through a telecoil or magnetic sensor;
    accessing data stored on the hearing assistance device representing the audio sample;
    playing the audio sample through a speaker of an external device; and
    prompting an individual to generate the audio sample.

6. The method of claim 1, wherein the operation of providing an audio sample to a hearing assistance device wearer comprises both
    streaming the audio sample to the hearing assistance device; and
    playing the audio sample through speakers of an external device.

7. The method of claim 1, further comprising qualifying the device wearer based on a severity of their hearing impairment or based on a perceived hearing handicap.

8. The method of claim 7, wherein qualifying the device wearer comprises presenting the device wearer with a panel of queries directed to the severity of their hearing impairment or their perceived hearing handicap and receiving feedback from the device wearer regarding the same.

9. The method of claim 8, further comprising estimating the severity of their hearing impairment or their perceived hearing handicap based on the device wearer's feedback.

10. The method of claim 7, wherein qualifying the device wearer comprises presenting the device wearer with a series of audio samples and questions regarding content of the same.

11. The method of claim 1, further comprising qualifying the device wearer based on settings for a previous device configured for the device wearer.

12. The method of claim 1, wherein qualifying the sound field comprises evaluating at least one of evaluating echoes, reverberation time, decay time, critical distance, room impulse measure, absorption coefficient across a human detectable frequency band, ambient noise, comb filter distortion, coloration distortion, early reflection, and late reflection.

13. The method of claim 1, wherein qualifying the sound field comprises emitting a sample sound and evaluating sound received at the hearing assistance device or an external device.

14. The method of claim 1, further comprising
    presenting the device wearer with a series of audio samples and questions regarding content of the same; and
    receiving answers to the questions from the device wearer.

15. The method of claim 14, further comprising calculating an accuracy score based on the received answers and initiating a corrective measure if the accuracy score crosses a threshold value.

16. The method of claim 15, the corrective measure comprising notifying the device wearer that they should contact a care provider and terminating the fitting procedure.

17. The method of claim 1, further comprising
recording speech from the device wearer; and
evaluating the recorded speech to classify a degree or configuration of hearing loss of the device wearer.
18. The method of claim 1, further comprising
determining a location of the device wearer;
evaluating regulations for device fitting based on the location; and
terminating or modifying the fitting procedure or notifying the device wearer that they should contact a care provider based on the regulations.
19. A hearing assistance device fitting system comprising:
a hearing assistance device comprising
a control circuit;
a microphone in electrical communication with the control circuit;
an electroacoustic transducer for generating sound in electrical communication with the control circuit;
a power supply circuit in electrical communication with the control circuit; and
an external device in wireless communication with the hearing assistance device;
wherein the system is configured to
provide an audio sample to a hearing assistance device wearer;
determine a degree of hearing impairment of the hearing assistance device wearer;
compare the determined degree of hearing impairment to a threshold level of impairment;
prevent the hearing assistance device wearer from continuing a device fitting process if the determined degree of hearing impairment is greater than the threshold level of impairment;
receive input from the hearing assistance device wearer;
receive input from the hearing assistance device wearer regarding a bass/treble balance; and
determine a maximum power output of the hearing assistance device that does not exceed a loudness discomfort level (LDL).
20. The hearing assistance device fitting system of claim 19, wherein the threshold level of impairment corresponds to a degree of hearing impairment that is severe or greater.

* * * * *